United States Patent [19]

Al Kasem

[11] Patent Number: 5,326,264
[45] Date of Patent: Jul. 5, 1994

[54] METHOD TO REINFORCE ENDODONTICALLY TREATED TEETH AND PASSIVE POST

[76] Inventor: Raed Al Kasem, 25 Donna St. #1207, Palm Harbor, Fla. 34684

[21] Appl. No.: 933

[22] Filed: Jan. 5, 1993

[51] Int. Cl.⁵ ............................................... A61C 5/02
[52] U.S. Cl. ..................................... 433/224; 433/220
[58] Field of Search ................ 433/91, 201.1, 220, 433/221, 224

[56] References Cited

U.S. PATENT DOCUMENTS

| | | | |
|---|---|---|---|
| 455,450 | 7/1891 | Fones | 433/221 |
| 825,940 | 7/1906 | Schuhman | 433/220 |
| 4,424,037 | 1/1984 | Ogino et al. | 433/173 |
| 4,483,678 | 11/1984 | Nishio et al. | 433/201.1 |
| 4,497,629 | 2/1985 | Ogino et al. | 433/201.1 |
| 4,645,457 | 2/1987 | Goldman et al. | 433/220 |
| 4,684,555 | 8/1987 | Neumeyer | 433/201.1 |
| 4,758,163 | 7/1988 | Goldman | 433/229 |
| 4,810,195 | 3/1989 | Asmussen | 433/213 |
| 4,830,616 | 5/1989 | Okuda et al. | 433/217.1 |
| 4,936,775 | 6/1990 | Bennett | 433/220 |
| 4,993,947 | 2/1991 | Grosrey | 433/81 |
| 5,062,798 | 11/1991 | Tsuge et al. | 433/201.1 |

FOREIGN PATENT DOCUMENTS

| | | | |
|---|---|---|---|
| 2370464 | 7/1978 | France | 433/91 |
| 22737 | of 1909 | United Kingdom | 433/220 |

Primary Examiner—John J. Wilson
Attorney, Agent, or Firm—Cushman, Darby & Cushman

[57] ABSTRACT

The present invention relates to a method for retaining a passive post and reinforcing endodontically treated teeth by coating a passive metal post with silicone and then with a resin coating, forming a post canal in a cavity, irrigating the post canal with a solution of Ethylene Diamine Tetracetic Acid, irrigating the post canal with Sodium Hypochloride, evacuating the post canal with a high vacuum suction tip, mixing and adding a cement comprising Bis-GMA and TEGDMA to the post canal, distributing the cement with a Lentulo spiral, inserting the silicoated metal post into the post canal, and holding the metal post under pressure until the cement sets. The invention also relates to vacuum apparatus for evacuating a post channel and dentinal tubules of moisture and to create an empty intertubular zone. The vacuum apparatus includes a vacuum suction tip having an outer diameter less than the inner diameter of the post channel and a high vacuum source connected to the vacuum tip. The invention further relates to a hexagonal shaped, parallel sided passive post. Surprisingly, the body of the remaining tooth structure is reinforced up to 30.3% and retention values similar to active posts are achieved by the method according to the claimed invention.

14 Claims, 11 Drawing Sheets

FIG. 3
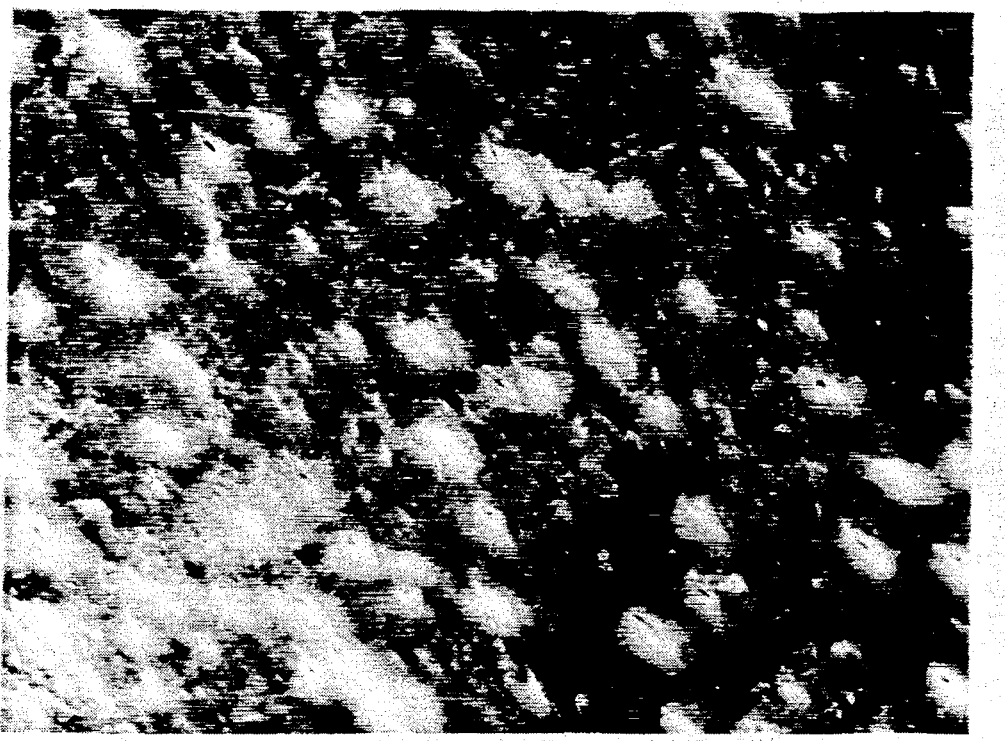
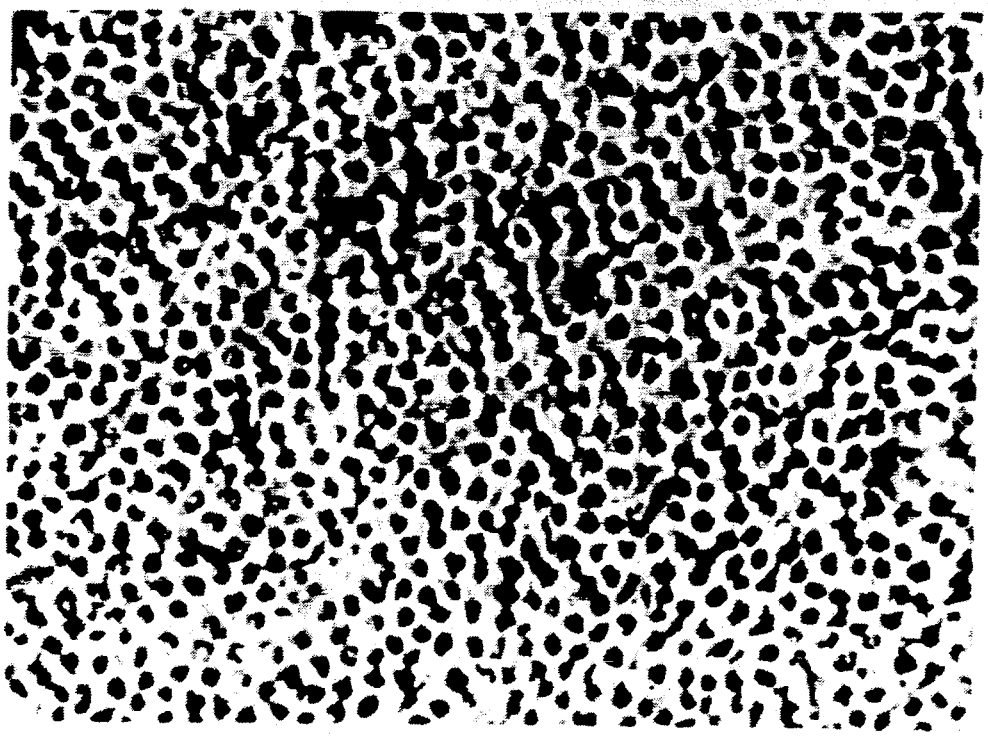
FIG. 4

FIG. 5
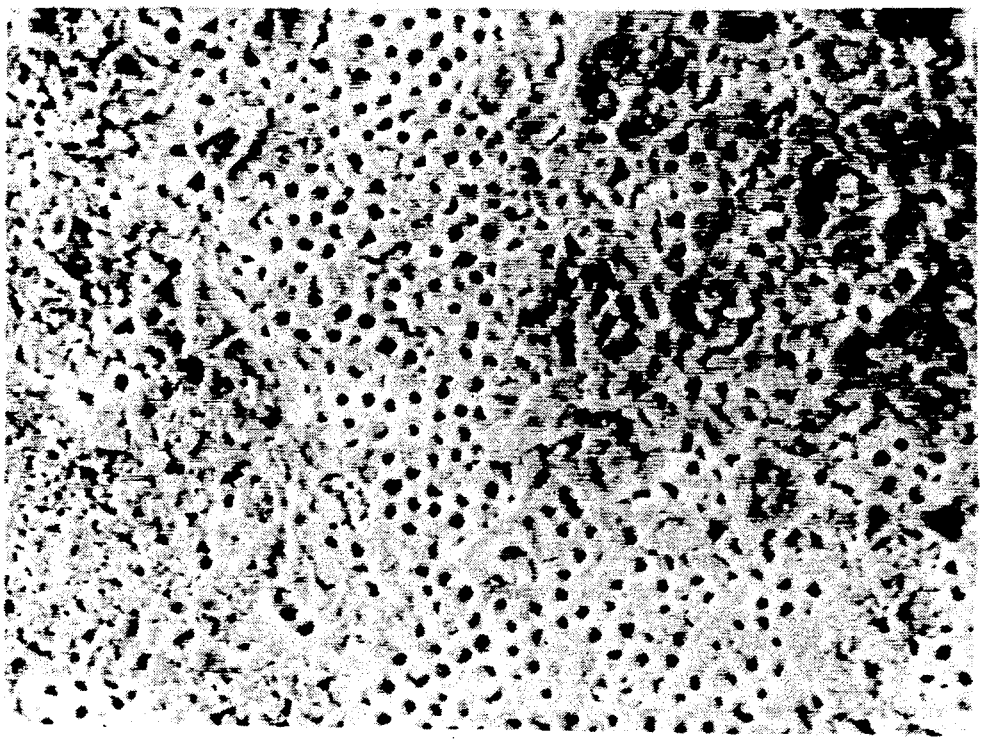
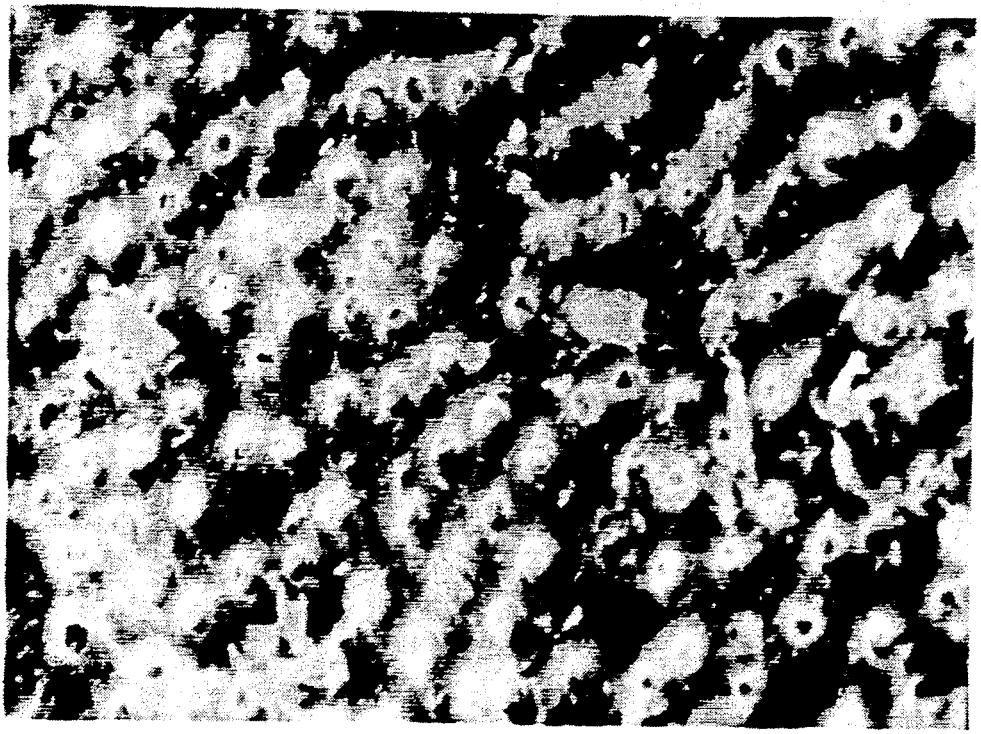
FIG. 6

FIG. 8
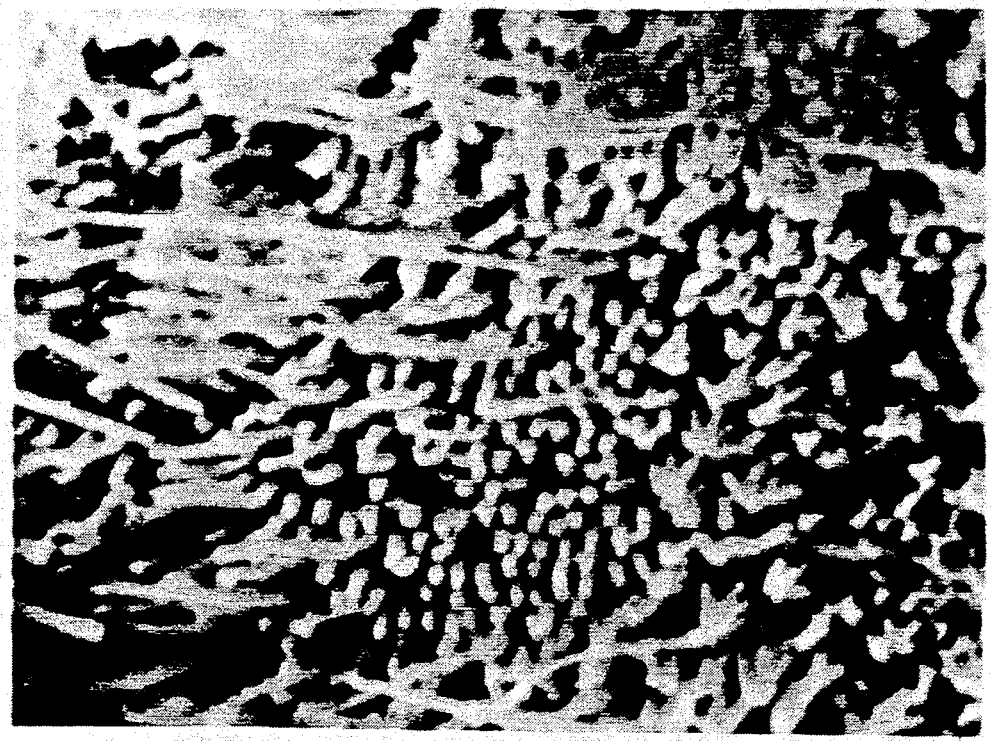
FIG. 9

FIG.10
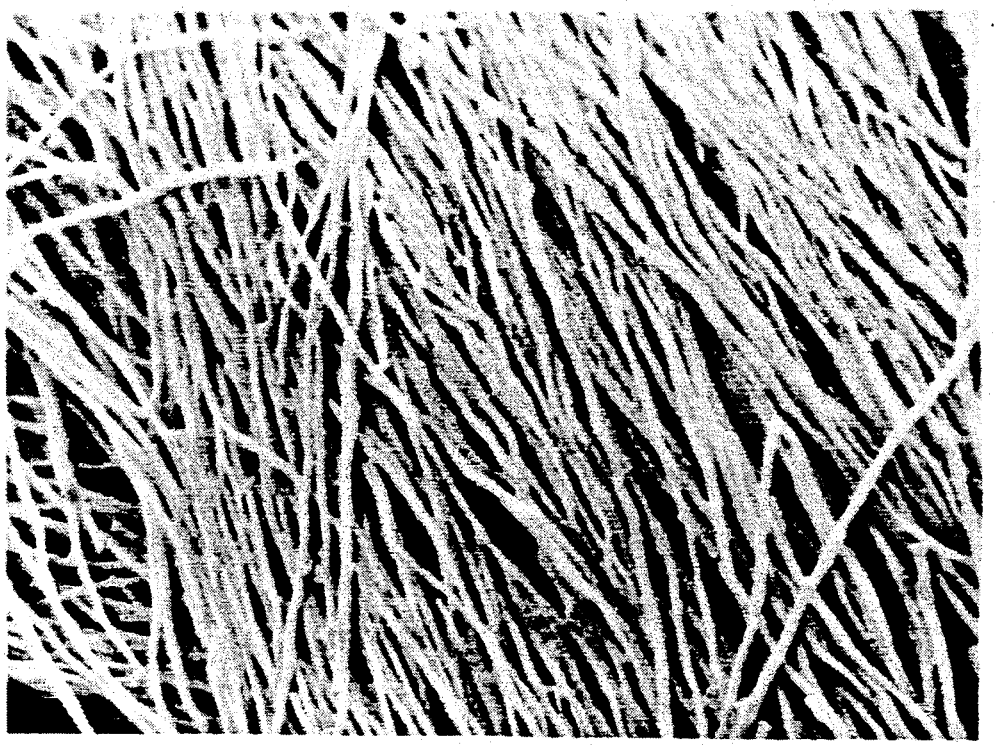
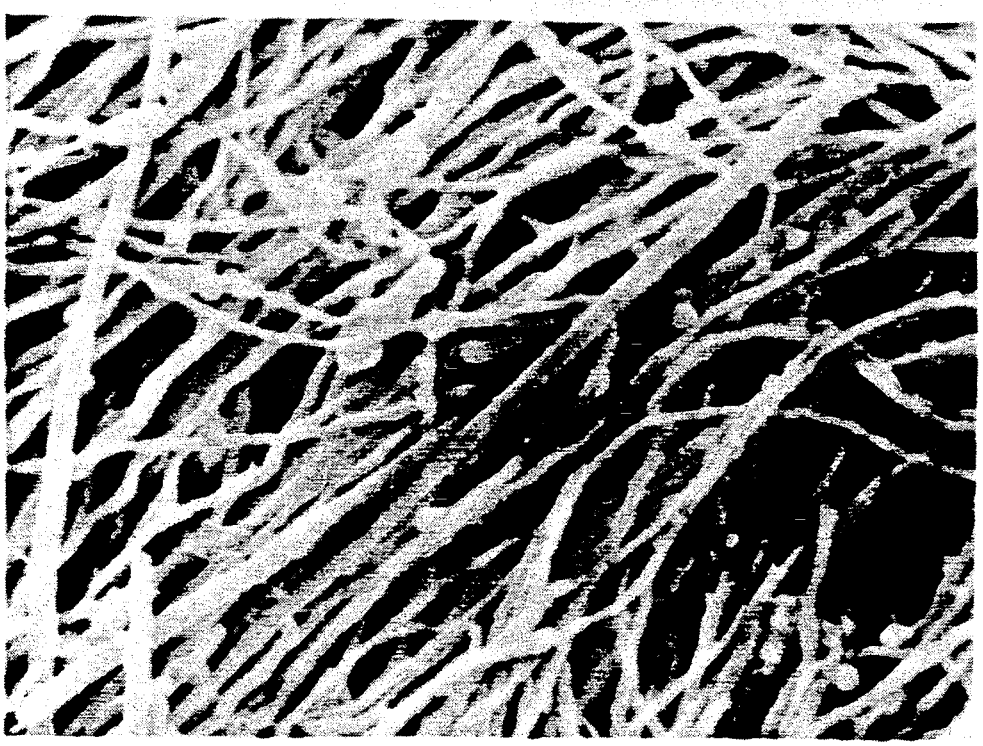
FIG.11

FIG.12
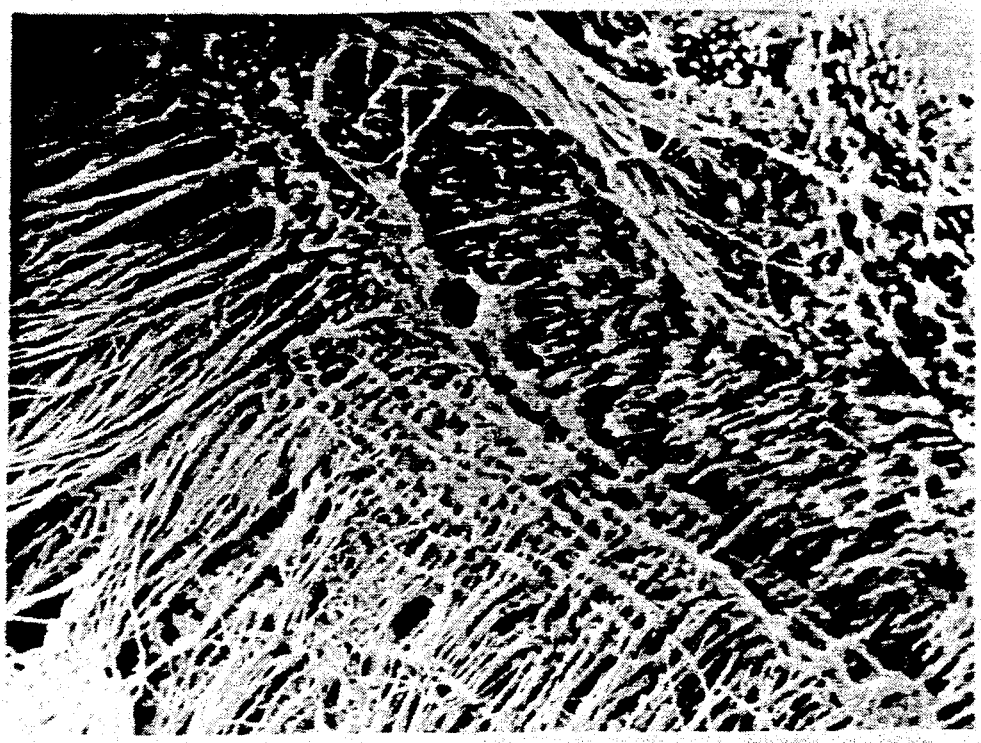
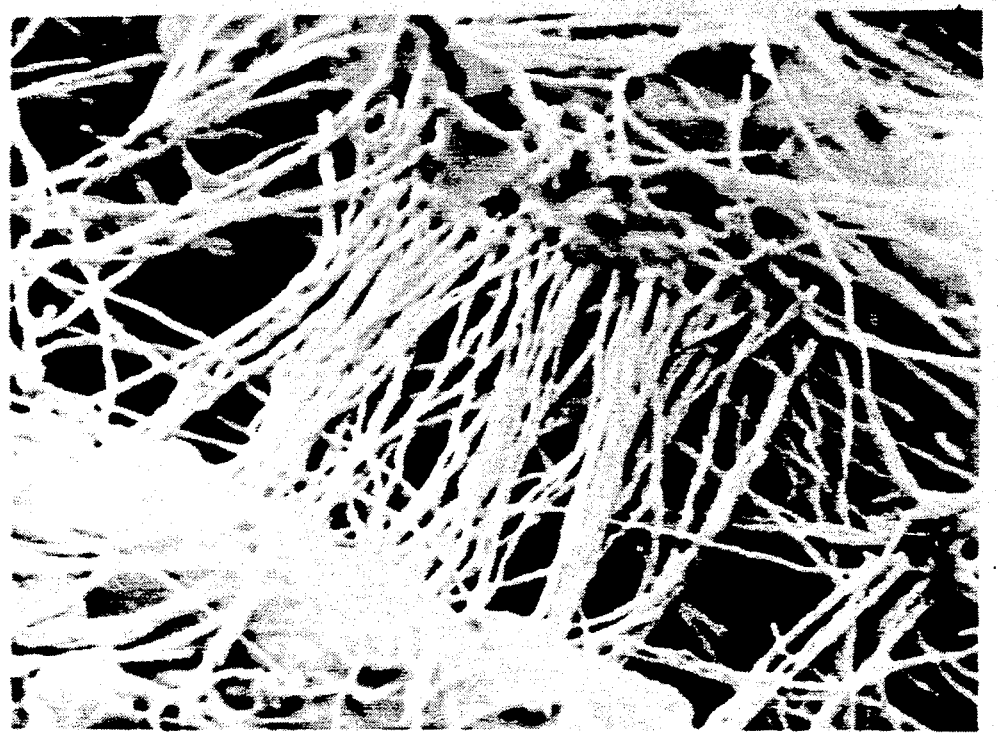
FIG.13

FIG.14
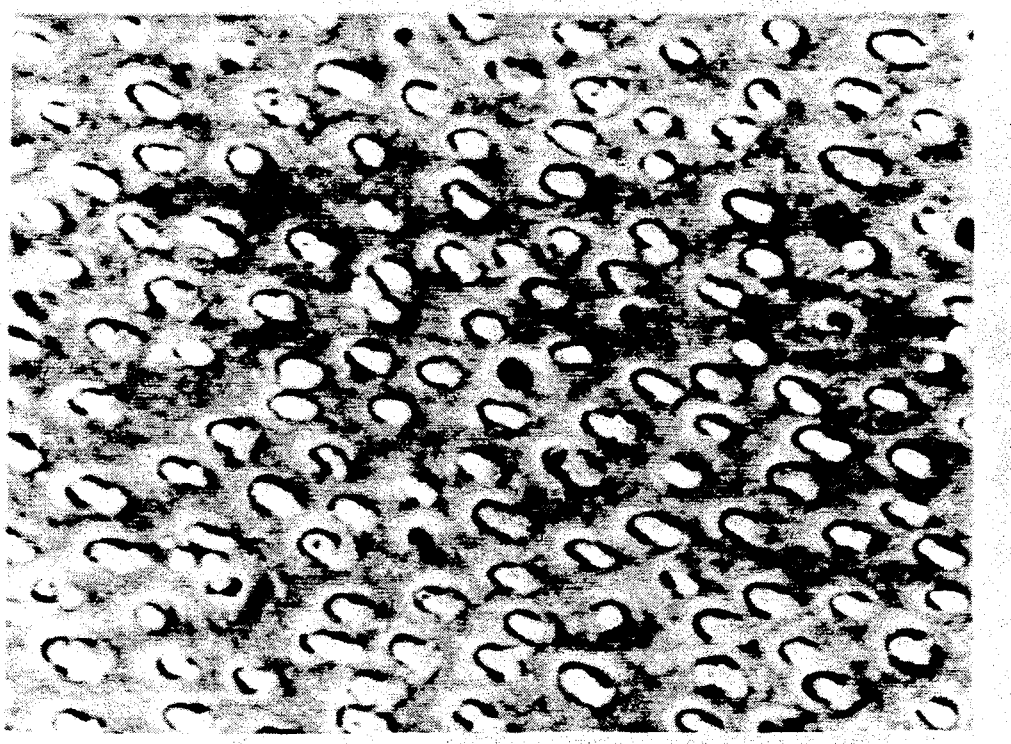
FIG.15

A: SiOx-C Boston Post-This Study-(B7)
B: SiOx-C Smooth Cast Post-This Study-(C5)
C: Boston Post -Nathanson (1988)
D: Parapost-Assif & Ferber (1982)
E: Parapost- Johnson (1978)
F: Boston Post - This Study
G: Parapost -Nathanson (1988)

METHOD TO REINFORCE ENDODONTICALLY TREATED TEETH AND PASSIVE POST

BACKGROUND OF THE INVENTION

1. Field Of The Invention

The present invention relates to a method for retaining a passive post and reinforcing endodontically treated teeth. The invention also relates to a specially designed vacuum apparatus for use in the method of retaining a passive post and reinforcing endodontically treated teeth. The invention further relates to a specially designed passive post for use in the method of retaining a passive post and reinforcing endodontically treated teeth.

2. Description Of The Related Art

The basic principals of root canal treatment are debridement, sterilization and obturation of the root canal. If these principals are successfully met, a positive prognosis is predicted for endodontically treated teeth.

However, there are situations when a successful root canal therapy is not enough to save an endodontically treated tooth from extraction. These situations are directly related to post-endodontic restoration, and, more specifically, when there is a need for intracoronal restoration.

Post designs, luting cements and status of remaining dentin have a great influence on the success of such a restoration. However, known post designs are made to fulfill the retentive needs of the coronal restoration and ignore the important need of the abutment root for reinforcement against fracture. This is especially true when the tooth has been weakened by caries, root canal treatment and post preparation.

Many factors have been documented that cause the root to split or fracture. Some of these include: dehydration of pulpless teeth, reduction of dentinal structure, reduced elasticity of dentin, stress from post design and cementation, corrosion of the metal post and residual stresses from lateral condensation of gutta percha.

One post design which has been found to have capabilities for protecting pulpless teeth against root fracture by distributing stresses evenly on the body of the root is the parallel-sided serrated post design.

Felton, D.A., Webb, E.L., Kanoy B.E., and Dugnoni J. (Threaded endodontic dowels: effect of post design or incidence of root fracture, (1991)) reported that the parallel-sided serrated post design's main disadvantage is the low retentive capabilities compared to most other post designs. Even with such design, some endodontically treated teeth may still carry the potential for root fracture, such as in the case of a large pulpal canal in immature teeth with little remaining dentin. Posting such teeth may lead to definite root split and eventually extraction.

Luting cements are used to fill the gaps between the post and surrounding channel walls. They play an important role in post retention and the distribution of stresses transferred through the post to the surrounding root structure.

No one type of cement has been found to have the overall ideal properties needed for cementing endodontic posts. One major problem of luting cements is their poor adhesion to the metal posts and to the surrounding tooth surface.

Removing the smeared layer which covers the channel walls and adding serration or irregularities to the post surface were found to be effective methods to increase the bonding between the luting cement and the post and the surrounding channel walls.

Silicoating the metal surface is a method that has been shown to be effective in bonding any metal surface to resin cement through an intermediate silane layer. This method is used in dentistry for bonding resin to the facial surface in crown and bridges and to cement Maryland bridges and metal rests to the tooth surface.

When an endodontically treated tooth requires a post restoration for the purpose of establishing a solid foundation for a permanent restoration, such as a crown, a post channel is first generated from the top access of the root canal deep into the middle third of the root canal, about 7 mm. This post channel is then occupied by a metal post cemented with a luting agent, such as Zinc-phosphate, Glass Ionomer or Composite Cement.

The commonly used luting cements have several disadvantages, such as poor bonding to the tooth surface surrounding the post channel and poor bonding to the metal surface of the post. The commonly used luting cements also have problems associated with solubility in water and oral fluids, and erosion and disintegration after long contact with oral fluids.

U.S. Pat. No. 4,936,775, discloses a luting cement comprising nexamethylene diisocyantate adduct of bis-GMA as a binder resin and triethylene glycol dimethylacrylate (TEGDMA) as the dilutent monomer.

The commonly used metal posts also have several disadvantages, such as corrosion which may lead to tooth fracture by the accumulation of corrosion products exerting pressure on the channel walls.

Known passive posts that fit loosely in the post channel and that are retained only from the surrounding luting cement have a low retention value, in the range of 70 to 80 pounds, which results in the potential for dislodgement.

Known active posts that have threads that engage the channel walls by being threaded or screwed in have high retention values, 170 to 190 pounds, however, these posts also exert pressure and stress on the root that may lead to root fracture.

There are two main reasons for using posts and cores: 1) to guarantee an appropriate foundation for the final restoration and 2) to distribute stresses from occlusal forces throughout the remaining tooth structure for the purpose of preventing tooth fracture, Caputo A.A., and Standlee J.P. (Pins and posts-why, when and how. *Dental Clinic of North America*, 20 299, (1976)).

According to Healey H.J. (*Endodontics*. St. Louis, The C. V. Mosby Co. pp 267-268 (1960)), the remaining coronal portion of the endodontically treated tooth is more brittle than when it contained vital pulp. Helfer A.R., Melnick S., and Schilder H. (Determination of the moisture content of vital and pulpless teeth. *Oral Surgery*, 34 (4), 661-669 (1972)) demonstrated that endodontically treated teeth contain 9% less moisture in the calcified tissues than do vital teeth. They concluded that once the moisture has been lost from calcified tissues, it can not be recovered.

Tidmarsh B.G. (Restoration of Endodontically Treated Posterior Teeth. *Journal of Endodontics*, 2 (12), 374-375, (1976)) compared a dehydrated pulpless tooth to a dry, dehydrated branch of a tree which "breaks easier than its living counter-part" (pp 374). Tidmarsh also states that an access opening as a part of endodontic treatment removes a very substantial part of the coronal dentin. Consequently, low loads may cause root fracture upon post insertion and may be related to the reduced thickness of dentin.

The use of radioactive phosphorus has demonstrated that the metabolic process in the pulpless teeth decreases rapidly in the coronal dentin. The study by Boyle P.E. (*Kronfeld's Histopathology of the Teeth*, ed. 4, Philadelphia, Lea & Febiger, (1955)), demonstrated that, as a result of pulp removal, there is a loss of elasticity as compared to the radicular dentin. As a rule, the root portion is less affected if there is normal functioning periodontal support. This may be one of the reasons that the cervical region of the root is more likely to fracture in endodontically treated teeth. Trabert, K.C., Caputo, A.A., and Abou-Rass M. (Tooth fracture, a comparison of endodontic and restorative treatment. *Journal of Endodontics*, 341-345, (1978)) and Guzy G.E., and Nicholls J.I. (An in vitro comparison of intact endodontically treated teeth with and without endo-post reinforcement. *Journal of Prosthetic Dentistry*, 42 (1), 39-44,(1979)) demonstrated this phenomenon in two separate studies.

One theory has suggested that the intact tooth with no cavity preparation behaves as a prestressed laminate, which withstands higher loads in an unstressed state. When the cavity is generated, it releases the stresses and destroys the prestressed state, leaving the tooth less resistant to fracture under elevated loads, Malcom P. (Cast restoration and cusp flexibility. Thesis of Otago Dunegin, New Zealand, (1973)).

On the question of whether or not endodontically treated teeth are less resistant to fracture, clinicians and researchers have been divided into two groups. One group suggests that the use of endodontic posts enhances the strength of the tooth; the other group believes that such treatment causes a reduction in strength.

Baraban, D.J. (The restoration of pulpless teeth. *Dental Clinics of North America*, 633-635, (1967)) recommended the use of a cast post as a reinforcement method for pulpless teeth. Perrell, M.L. and Murrof F.I. (Clinical criteria for post and cores. *Journal of Prosthetic Dentistry*, 28 405-411, (1972)) suggested that once a root canal has been performed on an anterior tooth, it must be reinforced with a post and core.

In a comparative study of restorative techniques for pulpless teeth, Kantor, M.E. and Pines, M.S. (A comparative study of restorative techniques for pulpless teeth. *Journal of Prosthetic Dentistry*, 38 (4), 405-412 (1977)) demonstrated that the use of prefabricated stainless steel posts, such as Parapost, actually reinforced the pulpless tooth and, in fact, doubled its resistance to fracture as compared to a pulpless tooth without posts. However, when they tested pulpless teeth restored with tapered gold cast posts, they observed that they were less resistant to fracture than the other two groups.

Another study was conducted by Leary, J.M. and Aquilino, S.A. (An evaluation of post length within the elastic limits of dentin. *Journal of Prosthetic Dentistry*, 57, (3), 277-281, (1987)) in which they applied a compression load at 90 degrees from the CEJ to the long axis of various experimental pulpless teeth groups. Their results indicated that if a tooth structure was removed from the tooth, it became weaker, and that teeth restored with post do show more reinforcement than non-posted teeth. Taylor, A.G. (Dowel abutment crown. *Royal Canadian Dental Corps Quarterly*, 4, 1-4 (1963)), Johnson, J.K., and Sakamura, J.S., (Dowel form and tensile force. *Journal of Prostetic Dentistry*, 40, 645-649 (1978)), Barum (1979); Waliszewski, K.J. and Sabola, C.L. (Combined endodontic and restorative treatment considerations. *Journal of Prosthetic Dentistry*, 40, 152-156 (1978)), Sapone, J., and Lorencki, S.F. (An endodontic-prosthodontic approach to internal tooth reinforcement. *Journal of Prosthetic Dentistry*, 45, 164-174 (1981)) and others also supported the idea of reinforcing pulpless teeth by using an endo-post.

Guzy and Nicholls, et al. (1979) compared breaking loads of endodontically treated teeth with and without posts cemented using zinc phosphate cement. The load was applied to the clinical crown at 130 degrees. Their results demonstrated that no statistically significant reinforcement was achieved by cementing Kerr endopost no. 100° into a sound endodontically treated tooth. Furthermore, a clinical study by Sorenson, J.A. and Martinoff, J.T. (Intracoronal reinforcement and coronal coverage: A study of endodontically treated teeth. *Journal of Prosthetic Dentistry*, 51 (6), 780-784, (1984)) generated results that showed no significant increase in resistance to fracture was gained with a post used as a retainer for crown restoration.

In another study, Trabet et al. (1978) used an impact tester to demonstrate that there was no difference in employed fracture resistance between teeth which had not received root canal treatment and endodontically treated teeth without posts. However, when teeth were restored with a stainless steel parapost, size 1.25 mm in diameter, an increased resistance to fracture was obtained. This resistance was not evident when parapost size 1.75 mm diameter was used in the study.

Currently, two types of posts are clinically used, cast posts and prefabricated posts. Although both types serve the same purpose, prefabricated posts have been found to have some advantages over cast posts. There is an economical advantage, in that most of the time they are made of stainless steel or non precious alloy. Also, a practical advantage is that treatment can be done in one visit. This approach is also more conservative because it does not require extensive removal of dentin and special tapering at the cervical level, Abou-Rass, M. (The prefabricated post selection and use in endodontic and restorative therapy. *Clinical Dentistry*, 4, Chap. 10B:1, (1985)); Miller, A.W. (Post and core systems, which one is best: *The Journal of Prosthetic Dentistry*, 48, (1), 27-38, (1982)).

In a clinical study involving 1,273 endodontically treated teeth, Sorrenson & Martinoff (1984) observed that the tapered cast post and core technique was most often used by dentists. Surprisingly, the clinical success of that technique (87.3%) was less than that of the endodontically treated teeth without intracoronal reinforcement (89.9%). In their investigation, the use of parallel sided, prefabricated or cast parapost was clinically successful (97.7%-100%). Success or failure in their study was based primarily upon whether or not the treated tooth had a non-restorable root fracture.

In their defense of the use of prefabricated parallel-sided posts over tapered cast posts, Sorenson & Martinoff explained that cast posts are commonly used because they follow the shape of conical or ribbon-shaped canals. Unfortunately, damage to the roots restored with this system was commonly observed. On the other hand, the use of prefabricated parallel-sided posts in conical or ribbon shaped canals requires a greater cement thickness; consequently, there was more dependance on the luting cement for retention.

The use of well adapted cast posts in their study resulted in some root fractures. Failure of prefabricated parallel-sided posts, on the other hand, was attributed to post dislodgement. Correspondingly, no damage to the root structure occurred. They concluded that resistance to root fracture was more important than post retention.

Factors that influence post retention are post design, the luting cement and the depth of posts.

Post design has been proved to be very effective on retention, Standlee, J.P., Caputo A.A., and Hanson E.C. (Retention of endodontic dowels: effect of cement, dowel length, diameter and design. *The Journal of Prosthetic Dentistry*, 39 (4), 401–405, (978)). Shillingburg, H.T., and Kessler, J.C. (Principles of restoration of endodontically treated tooth. Chicago, IL, Quintessence Pub. Co. Inc., 28, (1982)) concluded that surface configuration probably plays the single most important role in retention.

Posts can be classified according to their retention with surrounding dentin and gain their retention from dentinal threading. Passive posts do not engage dentin and are seated passively in their post channel. They gain their retention primarily from the surrounding cement medium, Musikant, B.L., and Deutsch A.S. (A new prefabricated post and core system. *The Journal of Prosthetic Dentistry*, 52 (5),631–634, (1984)).

Posts also may be classified according to their surface configuration. They may be parallel sided or tapered. Furthermore, they may be either serrated or smooth. Active type posts proved to exhibit the highest retentive values among all other post designs, Standlee et al. 1978; Cooley, I.T., Hampson E.L., and Lenman, M.L. (Retention of post crowns, and assessment of the relative efficiency of posts of different shapes and sizes. *British Dental Journal*, 124, 63–69 (1968)).

An active, parallel-sided, threaded post design provides the greatest retention. On the other hand, it generates stress on insertion and additional stress concentration under occlusal forces. Even though these forces may be distributed evenly along the entire length of the shank, they could lead to a root fracture. Longitudinal split in the long axis of the tooth has been observed in association with such a type of post design, Deutsch, A.S., Musikant, B.L., Cavallari, J., and Lepley, J.B. (Prefabricated dowels: a literature review. *The Journal of Prosthetic Dentistry*, 49 (4), 498–505, (1983)), Musikant & Duetsch 1984; Sorrenson, J.A., & Martinoff, J.T. (Clinically significant factors in dowel design. *The Journal of Prosthetic Dentistry*, 52 (1) , 28–35, (1984)) .

Active, tapered, threaded posts are less retentive than parallel threaded posts, but still provide higher retention than any passive post design (Musikant & Deutsch 1984). The problem with this type of post is that it exhibits a wedging effect and generates high shoulder stress concentration on the coronal area upon insertion and also under function, Deutsch et al. 1983; Standlee, J.P., Caputo, A.A. (The dentatus screw: comparative stress analysis with other endodontic dowel designs. *Journal of Oral Rehabilitation*, 9, 23–33, 1982. (1982)).

Durney, E.C. & Rosen, H. (Root fracture as a complication of post design and insertion: a laboratory study. *Operative Dentistry*, 2, 90–96, (1977)) reported that the torque required to insert tapered threaded post was almost 25% of the torque required to fracture a root. In the same study, parallel threaded post insertion was found to have no effect on root fracture. This finding was confirmed by Rivera, M. (The incidence of intraorganic fracture of brace roots. Master Thesis, McGill University, Montreal (1979)), who showed that tapered, self-threading posts tend to split teeth longitudinally during installation.

Passive posts are less retentive than active posts, because the luting cement plays a major role in their retention. The dislodgement of any passive posts occurs in response to shearing strain of the post-cement or dentin-cement interface (Standlee et al. 1978).

Passive parallel-sided posts have been shown to be far more retentive than tapered posts. This retention is increased if the post is serrated according to Cooley et al. (1968), Caputo and Standlee (1976), and Standlee et al. (1978). Musikant and Deutsch (1984) stated that parallel-sided passive posts distribute stresses evenly throughout the dentin, which then provides optimal protection against root fracture. The Parapost system is representative of this category, and it has become the most common type of prefabricated post used in restoration procedures.

Passive tapered posts are the least retentive posts especially when their surface is smooth. This design distributes stresses unevenly and acts like a wedge under occlusal loads, leading to increased stress concentration at the coronal part of the supporting dentin and may eventually lead to root fracture (Standlee et al. 1982; Musikant & Deutsch 1984).

Cooley et al. (1968) demonstrated that parallel-sided serrated posts cemented at a depth of 5.5 mm are more retentive than tapered posts at 8 mm depth. They also concluded that at least three factors influence retention strongly: the degree of post taper, the total involved surface area and lack of smoothness at the post surface.

In an in virto study dealing with endodontic posts, Chan, R.W. and Bryant, R.W. (Post core foundation for endodontically treated posterior teeth. *The Journal of Prosthetic Dentistry*, 48, 401 (1982)) used freshly extracted lower parallel-sided posts with amalgam or composite cores. Both groups were covered with full veneer crown. Their results showed that when a compressive load was applied to the veneered crowns, the cast posts and cores samples showed lower resistance and failed by post and core dislodgement or by root fracture. However, the prefabricated post samples showed higher resistance to dislodgement and fracture, and failed by amalgam or composite core fracture without causing the root to split.

Musikant and Deutsch (1984) generated the Flexi post design, which is an active, self-threading parallel post with blade-like threads characterized by a 7-mm split on the apical part of the post to compress upon itself during insertion, which then reduces insertion stresses and decreases chances of fracture. This design was meant to provide high retentive values while protecting remaining dentin from fracture.

Standlee, J.P., and Caputo, A.A. (The retentive and stress distributing characteristics of split, threaded endodontic dowels. *Journal of Dental Research*, 67 (Special Issue), Abstract 140, (1988)), in a photoelastic stress analysis study, demonstrated that the Flexi post exhibited minimal stresses during the insertion process, but under axial load, stresses were produced at each thread and at the coronal and apical levels. They explained that, as the shank of the post compressed, the parallel-shaped post actually becomes tapered and, consequently, produces a compressive stress on the walls of the chambers. They also demonstrated lower retentive values for the system in their study. Another study by Burns, A.A., Krause, W.R., Douglas, H.P., and Burns, D.R. (Stress distribution surrounding endodontics posts. *The Journal of Prosthetic Dentistry*, 64 (4), 412–418 (1990)) reported similar results, in that asymmetric patterns of stress distribution, stress concentration at each thread, greater shoulder stresses and substantial high stresses along the coronal surfaces were demonstrated for the Flexi post.

According to most of the reported investigation concerned with endodontic posts, the retentive values of all types of post designs can be listed in a decreasing order as follows: (active) parallel threaded, (active) tapered threaded, (passive) parallel serrated, (passive) parallel smooth, (passive) tapered serrated, (passive) tapered smooth.

Also, it has been documented that various types of posts produce different amounts of stress. In general in decreasing order they are: (active) tapered threaded, (active) parallels threaded, (passive) tapered and (passive) parallel.

From previous studies concerning post retention and reinforcement of tooth structure, it appears that no single post design is capable of producing high retention values, while at the same time providing maximum reinforcement for the endodontically treated tooth structure. Table 1 illustrates the shortcomings of known post design.

cement interface or the dentin-cement interface, regardless of the direction of masticatory forces. Consequently, the bond strength of any luting cement to dentin or post surface should have a substantial effect on the prognosis of the clinical success of the final restoration. Any luting agent should have the ability to provide the associated post with adequate retention in its prepared channel Standlee et al. (1978) also reported that the intensity, direction, frequency, and excessive forces on the endodontic post creates strains which could lead to root fracture, post fracture or post dislodgement. Another function for the luting cement is stress distribution. Perrel and Muroff (1972) indicated that the luting cement layer effectively redistributes the applied stress on the restoration to the surrounding dentin.

Leary J.M., Jensen, M.E., and Sheth, J.J. (Load transfer of posts and cores to roots through cements. *Journal of Prosthetic Dentistry*, 62, 298–302, (1989)) investigated the load transfer from cast posts and cores into the root through several luting cements. They demonstrated that the load was transferred extensively to the root, especially through zinc phosphate cement. This transfer was also observed with glass ionomer and Comspan cements but at lesser values.

Total stress in that study was measured before and

TABLE 1

| Post Design | Classification of main post designs | | | |
| --- | --- | --- | --- | --- |
| | Advantage | Disadvantage | Mode of Failure | Example |
| (Active) Parallel-sided threaded | Highest retention values | High stress under load at: the channel apex, the coronal level and around the threads. More stress at short length. | Longitudinal split on on the long axis of the root | Kurer Anchor Starr Dent. Mfg. Mfg. Co., Conshohoken, PA |
| (Active) Tapered, self-threading | High retention | Severe stress concentration during insertion and under load. Wedge-like effect. Tend to split roots. | Longitudinal split on the long axis of the root | Dentatus screw Dentatus, Stockholm, Sweden |
| (Passive) Parallel-sided serrated | Distribution of stress evenly, optimal protection for dentin. Provide for cement interlock | Lower retention values | Dislodgement with cement attached to the post | Parapost Whaladent, Int., NY |
| (Passive) Tapered smooth | Less stress concentration than active posts | Uneven stress distribution, wedge-like effect under load, lowest retention values, stress concentration at coronal level under compression load. | Dislodgement with cement left in post channel, root fracture | Custom cast post & Kerr endo-post Kerr Mfg. Co. |

Luting cements provide posts with retention. The cement serves as an intermediate agent, which distributes the generated stresses evenly throughout the root. The failure of endoposts is related directly to inadequate retention. If this retention is not provided through dentinal threading, as in active post systems, then the luting cement should have a significant role in post retention.

Excessive axial loads transferred to a cemented post, according to Maniatopulos, C., Pilliar R.M., and Smith, D.C. (Evaluation of shear strength at the dentin-endodontic post interface. *Journal of Prosthetic Dentistry*, 59 (6) 662–669, (1988)) leads to failure at the cement-post interface in smooth posts and at the cement-dentin interface in threaded posts. According to Standlee et al. (1978), dislodgement of posts from their channels occurs because of a shearing stress directed at the post-after post cementation. Results showed that the total stress had increased in the body of the tooth after cementation, and that it was distributed evenly along the surrounding root area. These results lead to a conclusion that luting cements, such as zinc phosphate, which provided a good adaptation between the post and the surrounding dentin, are capable of distributing the applied load uniformly from the post through the body of the root. The cement is also capable of protecting the root from localized high stress concentrations. This finding agreed with the photoelastic study by Caputo, A.A., Standlee, J.P., and Collard, E.W. (The mechanics of load transfer by retentive pins. *Journal of Prosthetic Dentistry*, 29, 442–449, (1973)).

Zinc phosphate cement is the most common luting agent used to retain endodontic posts. It has been used since 1900 and has become the standard to which new luting cements are compared. Zinc phosphate cement powder is composed mainly of zinc oxide plus 10% magnesium oxide, which serves as a modifier for the cement. The powder components are prepared by firing to 1400° C. prior to grinding into small powdery particles. The liquid in the cement is mainly 45-64% phosphoric acid plus 30-35% water, which is essential for the ionization. Aluminum phosphate is also added to the liquid as a buffer. As the powder and liquid are mixed, the phosphoric acid in the liquid dissolves the zinc oxide particles, while the aluminum ions help in forming a cohesive crystalline structure.

Zinc phosphate becomes a stiff cement after setting and resists elastic deformation. Its elasticity modulus is approximately $1.9 \times 10^6$ psi. In 24 hours the compressive strength of zinc phosphate reaches 15,000 psi, with a tensile strength of 800 psi. Due to its lower tensile strength, it is quite brittle. The film thickness of the cement is approximately 20 μm, Phillips, R.W. (Luting cements. Skinners science of dental materials 9th ed., pp 478-503, W.B. Sanders Co., Philadelphia, (1991)); Smith D.C. (Dental cements: current status and future prospects. *Dental Clinics of North America*, 6, (3), 763-792, (1983)).

One major problem with zinc phosphate cement is its solubility in water and oral fluids. Zinc phosphate is one of the most soluble of all luting cements, Phillips, (1991); Smith, (1983); Richer, W.A., and Veno, H. (Clinical evaluation of dental cement durability. *Journal of Prosthetic Dentistry*, 33 294, (1975)); Wilson, A.D., and Kent, B.E. (A new translucent cement for dentistry. The Glass Ionomer Cement. British Dental Journal, 132 (1972)). It is categorized as a temporary filling in restoring cavity preparations due to the erosion and disintegration of the material after long contact with moisture. The solubility of the cement in water ranges between 0.04 to 3.3% (standard 0.2%), and this solubility is increased dramatically up to 30% in organic acids, Phillips (1991), Craig, R.C. (Restorative Dental Materials 7th ed., St. Louis, The C.V. Mosby Co., (1985); Smith (1983)).

Another major problem with zinc phosphate is its lack of adhesion to the tooth structure. Phillips (1991) explained that the manner in which zinc phosphate functions as a retainer for a restoration is through its flow into the irregularities of the surfaces of the restoration and surrounding tooth structure, thus bonding by mechanical interlock. Consequently, if either surface is highly polished, the mechanical property of the cement drops down precipitously. Comb, E.C. (Cements, adhesives and non-metallic filling materials. *Notes in Dental Materials*, 5th ed., NY, Levingstone Inc., (1986)); Worley, J.L., Hamm R.C., and yon Fraunhoffer, J.A. (Effects of cement on crown retention. *Journal of Prosthectic Dentistry*, 48, 289-291 (1982)) and Chan, R.W., Azzarbal P., and Kerber, P.E. (Bond strength of cements to crown bases. *Journal of Endodontics*, 10 (8), (1981)) reported, for example, poor adhesion to tooth structure and metal restoration by zinc phosphate cement when compared to other cement materials.

Table 2 shows comparisons of properties of zinc phosphate, glass ionomer, polycarboxylate and silico phosphate cement.

TABLE 2

| | Comparison in properties of various luting cements decreasing order | | | | |
|---|---|---|---|---|---|
| Film Thickness (μm) | Compressive Strength (psi) | Tensile Strength (psi) | Modulus of Elasticity (psi × $10^6$) | Solubility & Disintegration (in vivo) | Adhesion |
| Zinc phosphate (20) | Silico phosphate (21,000) | Silico phosphate (1100) | Polycarboxylte (0.74) | Zinc phosphate | Polycarboxylte |
| Polycarboxylte (21) | Zinc phosphate (14,000-19,000) | Polycarboxylte (900) | Glass ionomer (1.06) | Polycarboxylte | Glass ionomer |
| Glass ionomer phosphate (25) | Glass ionomer (12,500) | Glass ionomer (900) | Silico phosphate | Silico phoxphate | Silico |
| Silico phosphate | Polycarboxylte | Zinc phosphate | Zinc phosphate | Glass ionomer | Zinc phosphate |

Information and data are taken from Phillips (1991), Craig (1987) and Smith (1983).

Although luting cements exhibit a wide variation of properties from material to material, studies which involved the use of different cements as luting agents for post retention have demonstrated that there is no correlation between post retention and cement type, Hanson, E.C., and Caputo, A.A. (Cementing medium and retentive characteristics of dowels. *Journal of Prosthetics Dentistry*, 32, 551-557, (1974)); Standlee et al. 1978; Krupp, J.D., Caputo, A.A., Trabert K.C., and Standlee, J.P. (Dowel retention with glass ionomer cement. *Journal of Prosthetic Dentistry*, 44, 163, (1979)).

Standlee et al. (1978) demonstrated that when zinc phosphate, polycarboxylate and epoxy resin were tested for the retention of a Parapost, the retentive values of these cements were not significantly different from each other. However, a significant increase in retention was obtained with zinc phosphate when a tapered smooth post was tested for retention. Epoxy resin was the least retentive cement in the study. It was pointed out in the same study that the luting cement always remained within the post channel whenever a tapered post was dislodged but under the same conditions the Parapost design allowed the cement to remain on the post surface.

Wood, W.W. (Retention of posts in teeth with non vital pulps. *Journal of Prosthetic Dentistry*, Dentistry, 49, (4) 504-506, (1983)) confirmed the findings of Standlee et al. in a study which involved testing tapered cast posts for retention, comparing zinc phosphate and composite resin as luting agents. Wood's results showed increased retention in favor of zinc phosphate cement over that of the composite resin. However, when retentive grooves were created in the post surface and adjacent grooves in the post channel, no difference was demonstrated in retention between zinc phosphate and composite.

Influenced by the reported adhesive properties of the polycarboxylate and the glass ionomer cement to dentin, Radake, W.A., and Veno H. (Clinical evaluation of dental cement durability. *Journal Of Prosthetic Dentistry*, 33, 294, (1988)) investigated the retention of the Parapost cemented with polycarboxylate, glass ionomer, zinc phosphate and composite resin. The results showed that the retentive values of glass ionomer and zinc phosphate cement were not significantly different from each other, but were higher than the retentive values of polycarboxylate and composite. Polycarboxylate cement was the next highest retention, while the composite resin showed the lowest retentive values in the study.

Chapman, K.W., Worley, J.L., and yon Frannhofer, J.A. (Retention of prefabricated posts by cements and resin. *Journal of Prosthetic Dentistry*, 54, 649-652, (1985)) also demonstrated that no changes in the retention values of Parapost were obtained by using zinc phosphate, polycarboxylate or glass ionomer cement. A difference in retention was shown when a strong posterior composite (P-10, 3M Company) was used as a luting cement. The retention values then dropped sharply. Chapman's conclusion was that the adhesion of the luting cement to dentin and post was more important than the shear strength of the cement itself.

Studies have shown that increasing the depth of the post provides an increased resistance to dislodgement. Cooley et al. (1968) demonstrated 2.23 times increased retention when the depth of the post was increased from 5.5 mm to 8 mm, while Standlee et al. (1978) showed a 1.5 times increase in retention.

Other studies showed different retention by changing the depth of the post, but all agreed that when the post depth in the post cavity preparation increases, the retention of that post also increases, Krupp et al. (1979); Johnson & Sakumara (1978); Ruemping, D.R., Lund, M.R., and Schnell, R.J. (Retention of dowels subjected to tensile and torsional forces. *Journal of Prosthetic Dentistry*, 41, 159-162, (1979)).

Hanson, E.C., and Caputo, A.A. (Cementing medium and retentive characteristics of dowels. *Journal of Prosthetics Dentistry*, 32, 551-557, (1974)) and Trabert, K.C., Caputo, A.A., and Hanson, E.C. (Effects of cement type and thickness on retention of serrated pins. *Journal of Dental Research*, 54, (2), 227-321, (1975)) pointed out that retention of any cemented post is affected by its adaptation to the post channel walls. A greater mismatch between the post and its channel results in decreased post retention. Chapman, K.W., Worley, J.R. and yon Frannhofer, J.A. (Effect of bonding agents on retention of posts. *General Dentistry*, 128-130, March-April (1985)) indicated that the luting cement's adhesion to dentin is more important than the shear strength of the cement.

Radake et al. (1988) tested several cements for the retention of an endo-post. They agreed that the bond strength of the cementing media plays an important role in the retention of the final restoration. Petters, M.C., Poort, H.W., Farah, J.W., and Craig, R.G. (Stress analysis of a tooth restored with a post and core. *Journal of Dental Research*, 62, 760-763, (1983)) also praised the post-cement bonding and reviewed it as the most important factor in achieving optimal mechanical behavior between the tooth and its restoration.

Chapman et al. (1985) reported that the use of resin as a luting cement is clinically acceptable. It can increase post retention, which then leads to a more conservative post cavity preparation as well as better preservation of the tooth structure. They added that the use of a bonding agent in conjunction with composite resin may add to the retention of the post.

Several authors relate the fracture of endodontically treated teeth to the corrosion of their posts in the root canal system. Rud J. and Omnel K. (Root Fracture Due to Corrosion. *Journal of Dental Research*, 78, 397-403, (1970)), in an in vivo study, inspected 468 extracted teeth that had failed due to root fractures. All teeth were restored with metal posts, cores and crowns. Their study showed that 71.8% of the fractures were related to pressure caused by corrosive agents. They indicated that corrosion most frequently occurred when the posts were made of stainless steel and contained tin. However, they recognized the capability of other metal components of causing corrosion. They also reported that if corrosion causes the root fracture, the fracture will always be vertical or oblique.

Dérand T. (Corrosion of screw posts. *Odontologic Revy*, 22, 371-378, (1971)) studied the in vitro corrosion of gold-plated Dentalus screw posts, which are composed mainly of copper and zinc with some gold and silver. His results showed that corrosion had occurred 10% of the time, and corrosion products penetrated into the dentin.

In 1969 Angmar-Manson, B., Omnel K.A., and Rud J. (Root fracture due to corrosion-metallurgical aspects. Odontologist Revy, 20, 244-265 (1969)) analyzed the corrosion products from posts and their relation to the restorative material. Their analysis showed that post materials were made of either stainless steel; German silver alloy (copper, nickel and zinc); brass (copper and zinc); gold alloy; or alloy of copper, zinc and silver. The core build-ups of the post, according to the study, were made of amalgam, silver, gold or cast alloy (tin, zinc and silver). Nineteen teeth exhibiting corrosion in their posts were involved in the study. The chemical composition of the corrosion products were mainly tin and/or zinc, and, in some cases, iron, chromium and copper were present. They indicated that once the tissue fluids penetrates through the luting cement, or after it has dissolved, a prolonged electrolytic reaction between the dissimilar post and core material occurs. This leads to corrosion of tin and the presence of corrosion products, which are not capable of diffusion through the dentin. Considerable pressure then is exerted and fracture occurs, attracting more fluid and oxygen, which speed up the corrosion process and a compact corrosion layer is formed around the post.

An extensive investigation was carried out by Silness, J., Gustavsen F., and Hunsbeth, J. (Distribution of corrosion products in teeth restored with metal crowns retained by stainless steel posts. Acta Ondotologic Scandinay, 37, 317-321, (1979)) on fractured teeth with corroded endodontic posts, involving the use of energy-dispersive X-ray microanalysis, microradiography and electron microscopy. The study involved fractured teeth previously restored with stainless steel posts with amalgam core and cast gold crowns. They observed that the posts and their channel walls were covered with corroded material. Iron and chromium, plus other elements of calcium, phosphorous, zinc and tin were routinely present on the main fracture surfaces. The dentinal tubules near the post channel were completely obliterated with a dense material consisting of the same elements. Iron and chromium are the main components of stainless steel posts, while tin and zinc exist in the amalgam core.

One important observation in the study by Silness et al. (1979) was the presence of a radiolucent area adjacent to the corrosion products. This finding suggested that a demineralization process had occurred, making calcium and phosphorus available, which then served as electrolytes for the corrosive process.

Patterson, K.B. (Longitudinal fracture due to corrosion of an endodontic post. *Journal of Canadian Dental Association*, 37, 66–68, (1971)) observed that longitudinal root fracture occurred in teeth restored with stainless steel posts, amalgam cores and cast gold crown. Arvidson, K. and Wroblewski, R. (Migration of metallic ions from screw posts into dentin and surrounding tissues. *Scandinavian Journal of Dental Research*, 86, 200, (1978)), also observed corrosion products in the dentinal tubules around the post and also in the gingiva adjacent to the fractured tooth. The extracted teeth in their study had been restored with posts and had fractured 3–10 years after the treatment.

Goldman, M., De Vitre, R. and Pier M. (Effects of the dentin smeared layer on tensile strength of cemented posts. *Journal of Prosthetic Dentistry*, 52, (4), 485–488, (1984)) evaluated the effect of removing the smeared layer on the retention of a parapost cemented with zinc phosphate, polycarboxylate and Bis-GMA resin cement. They observed increased retention in all cement groups: 38% for polycarboxylate cement, 40% for zinc phosphate and 126% for resin cement group. The significant increase in resistance to dislodgement was twice as great with the Bis-GMA cement group as it was with zinc phosphate, and the Bis-GMA cement group was found to be 3 times stronger than the polycarboxylate cement group.

In another study, Goldman, M., De Vitre R., White R., and Nathanson, D. (*Journal of Dental Research*, 63, (12), 1003–1005,(1984)) demonstrated the capability of Bis-GMA-based unfilled resin to penetrate the dentinal tubules after the smeared layer was removed. This penetration was of sufficient magnitude to suggest a strong mechanical lock due to the high compressive strength of the material.

The Boston post system was designed and patented in 1987 and 1988 as a result of Goldman's group studies. The Boston post is a stainless steel or titanium, parallel-sided, threaded post, which fits passively into its post channel, after a matching twist drill creates a post cavity preparation slightly larger than the post's diameter. Before the post is cemented, the post canal is rinsed with 2.5 ml of 17% EDTA followed immediately by 2.5 ml of 5.25% NaOCL before it is dried with paper points and compressed air. The luting cement in the system is chemically cured Bis-GMA based unfilled resin with a low viscosity which is claimed to have substantial adhesive properties. The compressive strength value also is claimed to be around 30,000 psi. The luting cement bonds to dentin and flows into the serration of the post to provide a strong retention after it sets.

The retentive properties of the Boston post system was tested in comparison with Flexi post and parapost, using each post's recommended luting cement. The three post groups were cemented at a depth of 7 mm, and the results obtained showed higher separation loads for the Boston post group (mean of 80.7 lbs), followed by the Flexipost group (mean of 75.9 lbs) and the lowest mean value, parapost (35.9 lbs). The advantage of this post technique could be increased retention at a shorter post channel depth, which could reduce the chances of perforation, Nathanson, D., and Ashayeri, N. (Effects of a new technique CDA Journal, 27–31, November (1988)); Nathanson, D. (New restorative concepts for posts and cores. *Journal of Clinical Dentistry*, 1, (2), 44–45, (1988)).

Endodontic treatment involves cleaning, disinfecting and shaping of the root canal in preparation for a successful obturation. As a result of the mechanical instrumentation against the dentinal walls of the canal, a smeared layer is formed. Since 1975, authors have observed and described this layer in the root canal as thin amorphous debris which covers the instrumented surface, tending to block the lumen of the dentinal tubules, Moodnik, R.M., Dorn, S.O. Fledman, M.J., Levy, J., and Borden, B.G. (Efficacy of biomechanical instrumentation: a scanning electron microscopy study. *Journal of Endodontics*, 2, 261–266, (1976)); McComb, D., and Smith, D.C. (A preliminary scanning electron microscopic study of root canals after endodontic procedure. *Journal of Endodontics*, 1, 328–342, (1975)). Eirich, F.R. (The role of friction and abrasion in the drilling of teeth. In *The Cutting edge: Interfacial dynamics of cutting and grinding*, Ed. Pearlman, S., DHEW publication No. 76-670, pp 1–49, (1976)) reported that the smearing occurs when the hydroxylapatite in the dentinal tissues is "either plucked out or broken or swept along the resets, in the smeared out matrix" (pp 1–49).

Further investigation of the root canal smeared layer revealed that it contains organic and inorganic components, and that its thickness ranged between 1–5 $\mu$m. Studies also have shown that this layer is not always firmly attached and not continuous with the dentinal surface, Gwinnett, A.J. (Smear layer: morphological considerations. *Operative Dentistry*, Supplement 3, 3–12, (1984)); Bränström, M. (*Dentin and pulp in restorative dentistry.* London: Wolfe Medical Publications Ltd., (1982)); Moodnick et al. 1976; and McComb, D., Smith, D.C., and Bengrie, G.S. (The results of in vivo endodontic chemomechanical instrumentation-a scanning electron microscopic study. *Journal of British Endodontic Society*, 9, 11–18, (1976)). One scanning electron microscopic study by Mader, C.L., Baumgartener, J.C., and Peters, D.C. (A scanning electron microscopic investigation of the smeared layer on root canal walls. *Journal of Endodontics*, 10, 477–483, (1984)) reported the smeared material to be about 1–2 $\mu$m in thickness, but was also found to be packed into the dentinal tubules for variable distances, sometimes up to 40 $\mu$m.

Several studies have supported the need to remove the smeared layer because it can block the antimicrobial intra-canal medicaments from entrance to the dentinal tubules, which then may harbor necrotic tissue and bacteria. Another reason for detaching this layer is to facilitate the penetration and adaptation of dental filling material into the tubules and the canal walls, Yamada, R.S., Annabelle, A., Goldman, M., and Peck, A.L. (A scanning electron microscopy comparison of a high volume final flush with several irrigating solutions: part 3. *Journal of Endodontics*, 9, (4), 137–142, (1983)).

Pashley, D.H., Livingston, M.J., Reeder, O.W., and Horner, J. (Effects of the degree of tubular occlusion on the permeability of human dentin in vitro. *Archives of Oral Biology*, 23, 1127–1133, (1978)); Pashley, D.H., Michelisch, V., and Kehl, T. (Dentin permeability: effects of smear layer removal. *Journal of Prosthetic Dentistry*, 46, 532, (1981)); White, R.R., Goldman, M., and Lin, P.S. (The influence of the smeared layer upon dentinal tubule penetration by plastic filling materials. *Journal of Endodontics*, 10, (12), 558–562, (1984)); and White, R.R., Goldman, M., and Lin, P.S. (The influence of the smeared layer upon dentinal tubule penetration by endodontic filling materials. *Journal of Endodontics*, 13, (1987)) demonstrated that the smeared layer can be a barrier to fluid and other substances. It also can prevent the entry of the root canal filling material into the dentinal tubules, thereby decreasing the bond strength and adaption. If a dental cement is applied to the smeared layer that covers the dentinal surface, and if this cement is tested for its bond strength, the mode of failure will be either between the cement and the smeared layer, or between the components of the smeared layer itself, Pashley, D.H. (Smear layer physiological consideration. *Operative Dentistry*, Supplement 3, 13-29, 1984)).

Several solutions have been tested for removing of the smeared layer. Application of phosphoric acid at a concentration between 30-65% can achieve good clinical results. It also dissolves the peretubular dentin in a short period of time and enlarges the lumens of the dentinal tubules efficiently, Bränström, M. and Nordenvail, K.J. (The effect of acid etching on enamel, dentin, and the inner surface of the resin restoration: a scanning electron microscopic investigation. *Journal of Dental Research*, 56, 917-923, (1977)). Gwinnett (1984) reported the successful effect of phosphoric acid on smeared layer but also indicted that "it appears to degrade the collagen matrix" (pp 9).

The smeared layer is calcific in nature. Therefore, it is reasonable to use a chelating agent such as citric acid, lactic acid or ethylene diamine tetracetic acid (EDTA). EDTA has been shown to be capable of decalcifying dentin at a depth of 20-30 $\mu$m in 5 minutes. It has also been shown not to have irreversible pathological effect on the adjacent vital tissues, which makes it preferable over a more harsh material such as phosphoric acid, Goldman et al. (1981); Fehr & Nygaard-Ostby (1963).

However, EDTA alone is not capable of removing the organic debris which is also found within the components of the smeared layer. Sodium hypoclorite (NaOCl) is an appreciably better organic tissue solvent than a chelating agent, but it has little effect on the mineral components.

Yamada et al. (1983) studied the use of 10 cc of 17% EDTA buffered to pH =7.7, followed by 10 cc of 5.25% NaOCl for removal of the smeared layer. Their results demonstrated a successful removal of the smeared layer over all of the root canal.

Curry, J.A., Bragotto, C., and Valdright, L. (The demineralizing efficiency of EDTA solution on dentin. I. Influence of pH *Oral Surgery, Oral Medicine, Oral Pathology*, 52, (4), 446-448, (1981)) reported that the maximal solubilization of calcium carbonate by EDTA can be accomplished at pH 7.3. Seidberg, B.H., and Schilder, P. (An evaluation of EDTA in endodontics. *Oral Surgery*, 37, 609 (1974)) showed that the action of EDTA stops once it reaches equilibrium with calcium ions in dentin, which means that EDTA has a self-limiting action.

Since the total volume of the root canal is fairly small, frequent refreshing of the EDTA within the canal was suggested to increase the exposed surface. This was proved to be more effective than one continuous application. When EDTA was applied in five increments for 3 minutes each, the results showed that the amount of dissolved mineral substances was twice that as when EDTA was applied in one increment for 15 minutes, Weinreb, M.H., and Meier, E. (The relative efficacy of EDTA, sulfuric acid and mechanical instrumentation in the enlargement of root canals. Oral Surgery, 19, 247-252 (1965)). Wu, J. (An in vitro investigation of pH changes of root environment after removal of the smear layer in endodontic treatment with calcium hydroxide. Masters thesis, UAB, Birmingham, AL (1988)) confirmed the successful removal of the smeared layer by irrigating the canal with 10 ml of 17% EDTA (pH =7.4) in 3 increments of 3 ml, 3 ml, and 4 ml, followed by 10 ml of 5.25% NaOCl.

Other methods of removing the smeared layer have shown favorable results, such as ultrasonic energized systems, which physically detach the debris from the root canal walls, followed by aspiration, Cunningham, W.T., Martin, H., Pellen, G.B., and Stoop, D.E. (A comparison of antimicrobial effectiveness of endosonic and hand instruments in R.C. therapy. *Oral Surgery*, 54, 238, (1982)). Cameron, J.A. (The use of ultrasound in the removal of the smear layer: a scanning electron microscopy study. *Journal of Endodontics*, 9, 289, (1983)) confirmed the efficacy of this system on removing the smeared layer.

Tidmarsh, B.G. (Acid-cleansed and resin-sealed root canals. *Journal of Endodontics*, 4, 117-121, (1978)), in an in vitro study, demonstrated the capability of a low viscosity unfilled Bis-GMA resin (used for fissure sealant) to penetrate the dentinal tubules at variable depth after the smeared layer had been removed.

Root canal plastic filling materials were introduced around 1984 for clinical use. Hydrophilic plastic (pHEMA) and silicon were applied as permanent root canal fillers after the smeared layer was removed. These fillings were tested to show their ability to penetrate the dentinal tubules (White et al. 1984 & 1987). White et al. (1987) also showed successful penetration into the tubules by other filling materials such as epoxy resin (AH26)+and zinc oxide and eugenol (Roth 801).

The number of dentinal tubules at 0.1-0.5 mm from the pulp ranges between 30,000-52,000/$mm^2$. The tubular diameter at the same distance lies between 4-6.4 $\mu$m (mean 2.5), while the tubular total surface area ranges from 9-42% (mean 22.1%). The diameter decreases gradually as the tubule approaches the dentin-cementum junction. It also decreases in a linear fashion within the root canal from the coronal dentin (44, 243/$mm^2$) to the apical root dentin (8, 190/$mm^2$), Garbeoglio, R., and Bränström, M. (Scanning electron microscopy investigation of human dentinal tubules. *Archives of Oral Biology*, 21, 355-362, (1976)); Pashely (1984); and Carrington, P.J., Morse, D.R., Furst, M.L. and Siani, I.H. (A scanning electron microscopic evaluation of human dentinal tubules according to age and location. *Journal of Endodontics*, 10, (8), (1984)).

Factors that may influence the flow of any filling material into the tubules include: tubular radius, hydrostatic pressure gradient, tubular length and the viscosity of the filling material, Pashley (1984).

Bowen, R.L. (Dental filling material comprising vinyl silane treated fused silica and a binder consisting of the reaction product of bisphenol and glycidyl acrylate. U.S. Pat. No. 3,066,112, November, (1962)) introduced Bis-GMA resin, which has a higher viscosity than methylmethacryalate (MMA) and exhibits lower polymerization shrinkage. This resin is composed of Bis phenol A and glycidyl methacrylate (Bis-GMA), with the two organic compounds reacting to form an oligomer. The resin contains two double bonds capable of additional polymerization through the use of an initiator and an accelerator.

The polymerized Bis-GMA is highly cross-linked due to the presence of dysfunctional carbon bonds, Craig (1981); Lambrechts & Vanherle (1983).

To lower the viscosity of Bis-GMA, a diluent monomer is used, such as triethylene gylcoldimethacrylate (TEGDMA), a monomer which allows extensive crosslinking to occur between the chains, leading to increased resistance to solvent, but with a higher polymerization shrinkage.

Polymerization of dimethacrylate monomers is initiated by free radicals which are generated by chemical activation between an initiator (benzoyl peroxide) and an activator (tertiary amine).

Most dentinal bonding cements contain a reactive group linked to the methacrylate group by an aliphatic chain. The reactive group is believed to bond either to the calcium ions in dentin or to the inorganic part of the dentin. Phosphate is used as a reactive group in the dentinal bonding agent most of the time, Bowen (1962): Phillips (1991); and Craig (1985).

If Bis-GMA unfilled resin is capable of penetrating the dentinal tubules and, perhaps at the same time, can achieve some type of bonding action to the dentin, as Boston post system claims, then this system's major weakness may be the low bond strength expected between the resin cement and the metal.

Bonding between the metal surface and resin can be achieved through mechanical retention or chemical retention. Mechanical retention is provided through irregularities or undercuts on the metal surface, while chemical bonding can be obtained through an intermediate layer which is fused to the metal surface or by a chemical adhesive containing a coupling agent that attaches resin to metal. Mechanical beads, metal mesh, pitted metal, perforation of metal surface, electrolytic etching and chemical etching are several means for mechanical bonding, ADEPT Report (Pertinent information on cosmetic, adhesive and restorative dentistry. ADEPT Institute, Santa Rosa, Calif., 2, 2:25-39, Spring, (1991)); Livaditis, G.J., and Thompson, V.P. (Etched casting: an improved retentive mechanism for resin-bonded retainers. *Journal of Prosthetic Dentistry,* 47, 52-58, (1982)); McLaughlin, G. (One hundred second etch technique for etched metal bridges. *Journal of Michigan Dental Association,* 64, 347-349, (1982)); Alsobrook, C.S., Murray, S.G., and Yates, L.J. (Bond strengths of acid-etched bridge retainers. *Journal of Pedodontics,* 8, 387-392 (1984)); and Hudgins, J.L., Moon, P.C., and Knap, F.J. (Particle roughened resin-bonded retainers. *Journal of Prosthetic Dentistry,* 53, 471-475, (1985)).

A successful interfacial chemical bonding can be achieved through a pyrogenic silanization technique, known as silicoating. This technique was introduced to the U.S. in 1985. In general silicoating is a method in which a glass-like layer (SiOx—C) is applied on a toughened metal surface. This layer is capable of chemically bonding to resin through an intermediate silane layer. A silane bonding agent requires substrate end groups such as Si—OH to achieve a chemical bond. These groups are not available on the metal surface. The silicate surface tends to bond successfully to resin and remains stable even in a high moisture environment. In pure $SiO_2$ glass, each Si atom is connected to four 0 atoms, and this rigid coupling gives the glass its property of brittleness.

In the silicoating technique, a carbon or hydroxyl group is incorporated into the molecule to provide a glass-like layer with decreased brittleness and increased elasticity, based on the concept of a SiOx—C layer. A modified surface is built up on a roughened metal surface (through sand blasting with 250 $\mu$m aluminum oxide) to achieve a very thin silicoated layer. This is done through a flame pyrolitic deposition process, molecule by molecule, in the 10-20 angstroms size range, which is very small compared to the roughness on the sandblasted surface (1/100-1/100 times). It is essential for this layer to be as thin as possible because the change in $SiO_2$ chemistry builds up strains in the broader region that increase as layer thickness increases.

The built-up SiOx—C layer is not sufficient for resin adhesion because the surface —OH group of $SiO_2$ does not bond directly to the methacrylate group in resin. A bonding agent of silane type is therefore used to react with the —OH group. This occurs by splitting off the methanol ($CH_3OH$), forming an Si—O—Si bridge. The remaining organic surface (methacrylate) is polymerized with the resin, making a chemical bond between the resin and SiOx—C possible.

After the silanizing layer is applied, it is either bonded directly to the restoration resin or protected by a structure such as the Dentacolor opaquer, which is capable of chemical binding later with the resin. The use of unfilled resin coating on the silanization layer improves the resin wetting, giving the resin smaller contact angles where it meets with the coated surface.

The internal structure of the bonding layer (which is polymerized in organic frame work) becomes t similar to that of $SiO_2$, leading to resistance to water sorption, Wilfred, B. (The adhesion of dental resins to metal surfaces).

Some properties of this system include: A resin-metal bond, free of marginal gaps, independent of metal type; A corrosion resistance adhesive bond by a very thin glass-like surface (0.1-1 micron) over the metal surface; and, A stable adhesiveness of glass surface to any metal.

Silicoater MD (Kulzer Inc., Irvine Calif.), a known silicoater system utilizes a primer Sililink (Kulzer Inc., Irvine CA) and an adhesive Siliseal (Kulzer Inc., Irvine CA). Sililink provides a metaloxide-dotted silicate layer, which is burned out on the sandblasted metal surface in the Silicoater MD (Kulzer Inc., Irvine CA) at a temperature of 600° C. An elastic SiOx-layer, which is a thin interference layer with the metal surface, is built up in the firing process. After the surface cools, Siliseal is applied, which is the adhesion silane that link the SiOx-layer to the opaquer or the resin.

Several studies have compared the effectiveness of the Kulzer Silicoater system with other resin-metal bond techniques such as Ultra etch, Immersion etch, Lee primer, Gold link and Cover Up. The Silicoater system showed higher bond strength values between the metal and resin over that obtained in any other system, regardless of the resin used. Silicoated samples also showed stability of their properties under moistened conditions and after thermocycling up to 4000 times, for 24 hours.

Scanning electron microscope evaluation confirmed that the adhesion between the resin and the metal surface is gap free. Silicoated specimens under tensile bond strength also showed a cohesive failure within the resin most of the time, while other techniques showed adhesive failure at the metal-resin interface, Caeg, C., Leinfelder, K.F., Lacefiled, W.R., and Bell W. (Effectiveness of a method used in bonding resins to metal. *Journal of Prosthetic Dentistry,* 64, (1), 37-41, (1990)); Naegeli, D.G., Duke, E.S., Schwartz, R., and Norling, B.K. (Adhesive bonding of composite resins to casting alloys. International Association for Dental Research, Abstract 798, Chicago, (1987)); Twesme, D.A., Lacefield, W.R., and O'Neal, S.J. (Effects of thermocycling, silicoating and etching on composite bonding to Cu, Au and Ni base alloys. International Association for Dental Research. Abstract 799, Chicago, (1987)); Kaiser, D., Malone W., Godoy, F., and Jones, T. (Three different retentive methods for the resin bonded retainer. International Association for Dental Research, Abstract 796, Chicago, (1987)); Belser, W., Bugnon, J., and Mayer, J.M. (Shear strength of resin bonded retainers using different retention/adhesion techniques. International Association for Dental Research, Abstract 137, Toronto, (1988)); and Norling, B.K., Murray, A.J., and Dal Santo, F.B. (Comparison of bond methods for veneering stainless steel crowns. International Association for Dental Research, Abstract 888, Toronto,(1988)).

By evaluating several studies and investigations related to posting systems and in relation to pulpless teeth, the following conclusions are reached.

Posts fail mainly because of the following: lack of post strength; lack of sufficient post retention within the root; and, root fracture.

Factors that induce root fracture include: dehydration of dentin by root canal treatment, heated endodontic pluggers, or heat from rotary instruments; reduction of the bulk of dentin by root canal treatment or post-cavity preparation; decreased elasticity of remaining tooth structure; residual stresses from lateral condensation of gutta percha, Felton, D.A., Webb, E.L., Kanoy, B.E., and Dugnoni, J. (Threaded endodontic dowels: effect of post design on incidence of root fracture, (1991)); stress from some post designs; hydraulic pressure during post cementation; endodontically treated immature teeth due to low mineralized dentin, less bulk of dentin and large canals, and larger and more dense dentinal tubules; corrosion of metal posts; and/or, Possible effect of $H_3PO_4$ cement on dentin.

An evaluation of post designs and systems used in dentistry reveals that no post system is capable of providing high retentive properties and at the same time providing the weakened endodontically treated tooth structure with sufficient reinforcement without loading the remaining tooth structure with additional stresses. The same conclusion is also applied to the luting cements because no cement showed an overall success in all categories.

One problem that clinicians face is restoring endodontically treated teeth with short roots is the inability to increase post depth to provide additional retention. It is generally recommended that threaded active posts be used in this case. However, studies have shown high concentration stresses associated with loading short posts even when they are passive in design.

Another problem is the large canals in immature teeth which receive endodontic treatment. The amount of remaining mineralized dentin is considerably less than that in normal mature calcified teeth. In addition, the volume of the tubular dentin area is much higher and may be approximately 42% of the total surface area. Restoration of such teeth with an endodontic post or even leaving the canal without any reinforcement can lead to root fracture and extraction.

In other words, if the protection of the root is to be considered, the only available post design is the passive parallel post. Unfortunately, this design has low retention values because its retention relies on luting cements which are shown to be far from ideal.

On the other hand, if the retention of the post is a main concern, then the active threaded post design is best. Irreversible damage to the root structure have been associated with this type of post.

Therefore, there is a need for a post system which is capable of providing high retention values without compromising the protection of the root, while reinforcing the remaining root structure against possible fracture.

SUMMARY OF THE INVENTION

The present invention relates to a method for retaining a passive post and reinforcing endodontically treated teeth without the above disadvantages.

The present invention also relates to a specially designed vacuum apparatus for use in the method of retaining a passive post and reinforcing endodontically treated teeth.

The present invention further relates to a a hexagonal shaped, parallel sided, passive post for use in the method for retaining a passive post and reinforcing endodontically treated teeth.

In the method for retaining a passive post and reinforcing endodontically treated teeth, a passive metal post is coated with silicone and then with a resin coating. A post canal is made in a cavity. The post canal is irrigated with a solution of Ethylene Diamine Tetracetic Acid and then irrigated with Sodium Hypochloride. The post canal is then evacuated with a high vacuum suction tip. A cement comprising Bis-GMA and TEGDMA is mixed and added to the post canal using a syringe. A Lentulo spiral is used to distribute the cement and help it penetrate into dentinal tubules. The silicoated metal post is then inserted into the post canal and held under pressure until the cement sets.

Surprisingly, the body of the remaining tooth structure is reinforced up to 30.3% and retention values similar to active posts are achieved by the method according to the claimed invention.

BRIEF DESCRIPTION OF THE DRAWINGS

FIG. 3 is a Scanning Electron Micrograph of a smeared layer on post channel wall after post cavity preparation, original magnification at X1000.

FIG. 4 is a Scanning Electron Micrograph of the successful removal of the smeared layer using the invention, magnification at X900.

FIG. 5 is a Scanning Electron Micrograph of a partially removed smeared layer on the post channel wall after treatment by method 1, magnification at X750.

FIG. 6 is a Scanning Electron Micrograph illustrating the dentinal orifices still occluded with some debris from the smeared layer after treatment by method 1, magnification at X1000.

FIG. 8 is a Scanning Electron Micrograph showing limited penetration of resin tags (tooth dissolved by using 5% HNO3 and 5.25% NaOCl) after the smeared layer was treated by using method 1, magnification at X740.

FIG. 9 is a Scanning Electron Micrograph showing the variable depth of penetration of resin tags (tooth dissolved by using 5% HNO3 and 5.25% NaOCl) after smeared layer was removed by using method 2 and post cavity was not dried using the specially designed high vacuum suction tip at magnification X100.

FIG. 10 is a Scanning Electron Micrograph showing the successful penetration of resin tags (tooth dissolved by using 5% HNO3 and 5.25% NaOCl) after smeared layer was removed by using method 2 and post cavity was dried using the specially designed high vacuum suction tip at magnification X600.

FIG. 11 is a Scanning Electron Micrograph showing the successful penetration of resin tags (tooth dissolved by using 5% HNO3 and 5.25% NaOCl) after smeared layer was removed by using method 2 and post cavity was dried using the specially designed high vacuum suction tip at magnification X1000.

FIG. 12 is a Scanning Electron Micrograph showing areas of shallow penetration of resin on the apical third, original magnification at X180.

FIG. 13 is a Scanning Electron Micrograph showing bridges of resin tags between the unfilled resin luting cement and dentin, original magnification at X760.

FIG. 14 is a Scanning Electron Micrograph 1-mm away from the post channel showing tags filling the lumens of the dentinal tubules in several areas along the root, original magnification at X1000.

FIG. 15 is a Scanning Electron Micrograph 2-mm away from the post channel and approximately 0.3 mm from the dentinal-cementum junction showing resin tags occupying the lumens of the dentinal tubules, mostly in the cervical level, original magnification at X600.

DETAILED DESCRIPTION OF THE PREFERRED EMBODIMENTS

The metal post of the present invention is a passive post design which fits without any friction against the channel walls.

The post surface is first treated and then coated with a glass-like surface, in a process known as silicoating.

An example of a silicoating process that can be used in the present invention comprises sandblasting the metal surface, cleaning the metal, coating the clean metal surface in a pyrogenic process with the glass-like surface $SiO_x$, and then coating the silicoated surface with a resin layer.

Coating the clean metal surface with a glass-like surface can be accomplished by using, for example, a silicoater machine by Kulzer Inc., Irvine, Calif.

A post channel is then generated in the dentin.

The diameter of the post is preferably slightly smaller than the post channel, such as from 0.1 to 0.2mm smaller.

After the post channel is generated, the cavity is irrigated with two solutions, Solution 1 and Solution 2, for a specific time and frequency.

Solution 1 comprises about 17% Ethylene Diamine Tetracetic Acid (EDTA) having a PH of about 7.5. Solution 1 is applied to the canal in 3 increments, two of about 1.5 ml, and one of about 2 ml. Each increment is left in the canal for a period of about 1 minute, with an overall time of about 3 min.

Solution 2 comprises about 5.25% Sodium Hypochloride (NaOCl). Solution 2 only follows solution 1. The canal is irrigated with about 5 ml of Solution 2 for about 2 minutes.

Solutions 1 and 2 remove the debris area covering the walls of the post channel (smeared layer) and also expose the openings of the dentinal tubules which extend sideways from the root canal to the dentinal-cementum junction, adjacent to the outer surface of the root.

Figure 1:
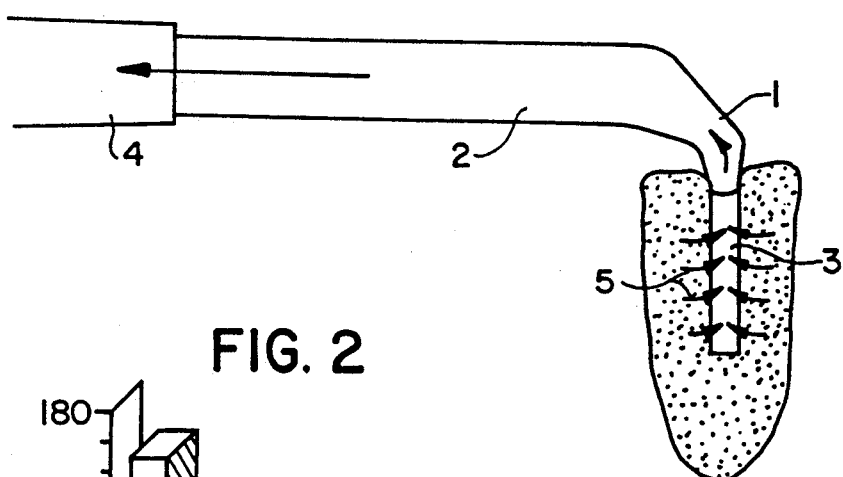
FIG. 1 is a diagram illustrating a specially designed high vacuum suction tip.

After the channel is irrigated, a specially designed high vacuum suction tip (1), shown in FIG. 1, is introduced to the opening of the canal, for the purpose of evacuating the post channel (3) and also the dentinal tubules (5) of any moisture, and to create an empty intertubular zone.

The high vacuum suction tip (1) is connected to a suction tube (2) and a high vacuum source (4). The high vacuum suction tip (1) preferably has an outer diameter less than the inner diameter of the post channel (3).

The luting cement, Chemical Cure Bis-GMA and TEGDMA based unfilled resin having high compressive strength values and low viscosity values, is then prepared. The base and the catalyst is mixed and then carried to the post channel, preferably with a syringe.

Preferably a lentulo spiral (rotating instrument) is then used to distribute the cement and also increase the penetration of the cement into the dentinal tubules.

The silicoated metal post is then inserted into the channel and kept under pressure until the cement is set.

The unfilled resin used for this technique has shown deep penetration into the dentinal tubules and to reach the boarders of the cemento-dentinal junction. The following factors effect this penetration: the evacuation of tubules from debris and moisture; and, the low viscosity value of the cement which provides deep penetration into the tubules by the capillarity of the tubules and by the pressure generated by the lentulo spiral.

Once this cement is chemically set or cured, the tooth structure is surprisingly reinforced and shows an unexpected increase in resistance to fracture of up to 30.3%.

The cement also activates the protection layer of the coated metal surface cement via the silicoated layer. As a result of this strong bonding, the retention values obtained by using the above technique was in the range of 172 pounds, which unexpectedly exceeds any retention values of any known passive posting techniques. This technique surprisingly provides retention values similar to the threaded (active) type posts without endangering the tooth structure and also shows a 30.3% increase in resistance to fracture.

Another advantage of this technique is that the post coating prevents the post from corrosion.

Figure 18:
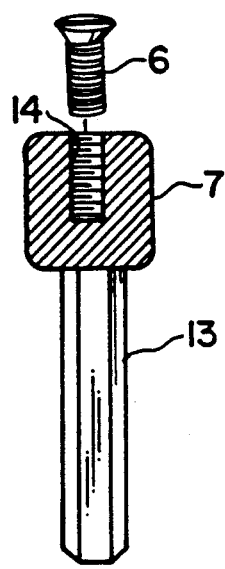
FIG. 18 illustrates one embodiment of a passive post according to the invention.
Figure 19:
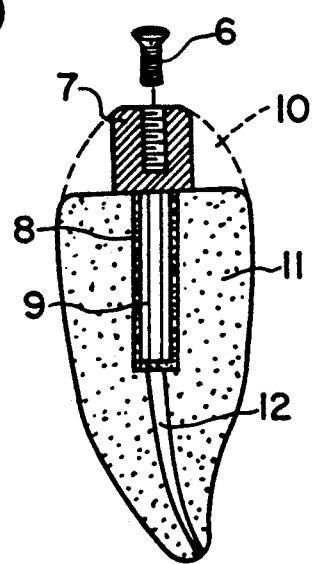
FIG. 19 illustrates one embodiment of a passive post according to the invention mounted in a tooth cavity.

Preferably the post is a hexagonal shaped, parallel sided, passive post, as shown in FIG. 18. FIG. 19 illustrates the hexagonal post fitted within the root dentin (11) and the location of hexagonal post relative to the root canal (12).

The six corners (13) of the post minimize friction and scratching of the silicoated surfaces against the post channel walls (9) during the fitting of the post. The hexagonal shape also prevents the post from rotating within the luting cement (8).

The total length of the hexagonal post is preferably between about 12 mm to 20 mm. A coronal top part (7) of the post is preferably about 5 mm to 7 mm of the total length of the post. The coronal top part of the post is preferably about 1 mm to 2mm wider in diameter than the diameter of the post.

The center part of the coronal portion preferably has about a 4 mm deep serrated groove (14), parallel to the long axis of the post, and open to the top surface of the post. The groove is preferably about 0.5 mm to 1 mm in diameter and designed to allow a matching screw (6) to be fitted and locked into the post.

The entire body of the post is preferably silicoated so that the apical part will bond to the luting resin cement and the coronal part may be used to enhance the bonding of a resin based filling or core buildup (10) to achieve maximum retention.

The serrated groove and the locking screw can also be an additional retention for a possible cast post and core so that the final restoration covering the coronal part of the post may be locked into the body of the post.

The advantages of the present invention are illustrated by the following studies.

Post Retention Study

Samples in the post retention study were subjected to tensile strength forces applied to the uncemented, free part of the post until it was dislodged from the channel. The resistance of each post to dislodgement until failure was documented and later analyzed statistically.

One hundred and twenty freshly extracted, single-rooted anterior teeth were collected from the Department of Oral surgery at UAB School of Dentistry, and stored immediately in physiological saline solution. Attached calculus, soft tissues and bone were removed from each tooth. All teeth were individually inspected to guarantee the absence of fracture, carries or resorption.

The crown of each tooth was subsequently separated from its root at the cemento-enamel junction, using a separation disc at a low speed rotation and constant water irrigation.

A root canal procedure was performed on each sample using a series of K-files in increasing order, starting from size #10 and ending with size #50.

A solution of 5.25% sodium hypochlorite was used as an irrigant during the root canal instrumentation.

Each root canal was filled by lateral condensation using gutta percha size #50 and a Grossman sealer. Immediately after condensation, a heated endodontic plugger was used to remove the gutta percha from the access opening down to a depth of 8 mm into the canal. All samples were divided randomly into 12 groups, with 10 samples in each group.

Due to the need for proper alignment of each sample during testing, it was necessary to make the coronal top surface vertical to the long axis of the post channel. To do so, each sample was cemented temporarily with sticky wax in a specially designed device. This device consisted of a 2"×2" clear acrylic block with parallel sides. The post in each channel was positioned so that the post could be removed from it channel along a parallel axis to the top surface of the device. The device was placed in a high speed cutting machine and a vertical cut through the post channel at the first millimeter of the coronal upper surface was made. The post cavity preparation in each sample was then checked and adjusted to attain a 7-mm total length.

Independent variables tested in this study were: post design, post surface treatment, luting cement, and smeared layer treatment.

Two types of passive posts were tested: prefabricated Boston post (Roydent Dental Products, Troy, Mich.) (parallel-sided & serrated) and cast post (parallel-sided & smooth). All posts were of equal dimensions (1.6 mm diameter) and differed only in surface design. Both posts matched the channel created by a Boston post twist drill (1.6 mm diameter) and were seated without lateral movement and with minimal frictional binding at depth of 7 mm.

Cast posts in this study were made by casting size 14 plastic Williams spruces (Williams Dental Co. Inc., Buffalo, N.Y.). They were spruced in five groups of 10 specimens, and cleaned with a wax pattern cleaner (Jelenco Products, Armonk, NY), then invested in 5 cast rings using Complete Investment powder and solution (Kulzer Inc., Irvine, CA). An induction casting machine was used to fabricate the Ni-Cr base alloy (WellCeram, Lite-Cast B alloy) according to the manufacturer's recommendations. The posts were then cut from their spruces, and their surfaces were cleaned by using a series of stone burs. Each completed post was evaluated for fit in the prepared post channel.

The surfaces of the Boston posts and cast posts were either silicoated or left without surface treatment.

The silicoating procedure included sandblasting each post using a 250 $\mu$m aluminum oxide at 90 psi for 15 seconds. Posts were then cleaned ultrasonically and with a soft tooth brush using a solution of Siliclean (Kulzer Inc., Irvine, CA), then dried for 5 minutes. An ultra thin layer of Slilink (Kulzer Inc., Irvine, CA) was painted onto the surface of each post using a small soft brush. The posts were then placed in the Silicoater MD (Kulzer Inc., Irvine, Calif.) at a setting designed for non-precious alloys for a time of 8 minutes. The posts were then removed from the Silicoater and allowed to cool for 4 minutes. A coat of Siliseal (Kulzer Inc., Irvine, Calif.) was applied to the posts and allowed to dry to 2 minutes. A thin protecting layer of Dentacolor (Kulzer Inc., Irvine, Calif.) was then put on the posts. The posts were then photocured in a Kulzer XS photo-cure unit for 90 seconds.

The luting agents used in this study included zinc phosphate cement and Boston post resin cement. Before cementing each post, the smeared layer on the post channel walls was either treated by EDTA and NaOCl, as recommended by Boston post manufacturers, which will be referred to in this study as method 1, treated by the technique according to the present invention, which will be referred to as method 2, or left untreated.

Method 1: The post channels were irrigated with 3 ml of 17% Ethylene diamine tetracetic acid (EDTA) at pH 7.5, followed immediately by 3 ml of 5.25% sodium hypochlorite NaOCl.

Method 2: the post channels were irrigated with 5 ml of 17% EDTA in 3 increments of 1.5 ml, 1.5 ml, and 2 ml, 1 minute each, for a total of 3 minutes, followed by 5 ml of 5.25% NaOCl for one minute.

Each channel was dried and evaluated after irrigation by using a specially designed suction tip, shown in FIG. 1. Next, an air syringe was used to direct compressed air into the channel for 10 seconds.

Cementing with zinc phosphate cement was carried out in accordance with the manufacture's recommendations. The cement powder and liquid were mixed to a creamy consistency. The cement was introduced into post channels with a #50 K-file. A lentulo spiral was used to coat the surface of the posts channel with cement. The posts were also lubricated with the cement to ease their insertion into the prepared channels. Each post was held in position with a constant pressure for 10 minutes.

Cementing with Boston post resin was carried out according to the manufacturer's recommendations by mixing equal amounts of cement A (base) and cement B (catalyst) for 10 seconds. The mixture was transferred with a disposable syringe into the post channels. A lentulo spiral at low speed rotation was used to distribute the cement into each canal. Posts were then covered with the cement before they were inserted into their channels and then subjected to constant pressure for 10 minutes. Working time was approximately 1 ½ minutes followed by a setting time of 2-3 minutes.

All restored samples were soaked in a water-containing sponge for 1 hour and then stored in a physiological saline for 24 hours. They were then thermocycled 500 times in water at temperatures of 8° C. to 50° C., using a dwell time of 15 seconds at each temperature.

For the sake of simplicity, the post retention study was divided into Boston post groups test and results and into cast post groups test and results. A list of the variables used in this study are shown on Tables 3 and 4.

TABLE 3

Experimental design for boston post retention study

| Group | Samples | Surface Treatment | Cement | Smeared Layer |
|---|---|---|---|---|
| B1 | 10 | — | $ZnPO_4$ | intact |
| B2 | 10 | — | $ZnPO_4$ | treated by method 1 |
| B3 | 10 | — | $ZnPO_4$ | treated by method 2 |
| B4 | 10 | — | Unfilled Resin | intact |
| B5 | 10 | — | Unfilled Resin | treated by method 1 |
| B6 | 10 | $(SiO_x)$ | Unfilled Resin | treated by method 1 |
| B7 | 10 | $(SiO_x)$ | Unfilled Resin | treated by method 2 |

TABLE 4

Experimental design for cast post retention study

| Group | Samples | Surface Treatment | Cement | Smeared Layer |
|---|---|---|---|---|
| C1 | 10 | — | $ZnPO_4$ | intact |
| C2 | 10 | — | $ZnPO_4$ | treated by method 2 |
| C3 | 10 | — | Unfilled Resin | treated by method 1 |
| C4 | 10 | $(SiO_x)$ | Unfilled Resin | treated by method 1 |
| C5 | 10 | $(SiO_x)$ | Unfilled Resin | treated by method 2 |

A stainless steel jig was designed for this study, and used to mount each sample in an Instron Universal testing machine (Instron Corp., Canton, Mass.). This jig mainly consisted of two horizontal stainless steel bars, parallel to each other and connected by two steel screws. The lower bar possessed a slot, which allowed the uncemented part of the post in each sample to hang free, while the coronal surface of the tooth around the post was held by the bar. The upper jaw of the Instron machine gripped a steel screw attached to the top bar of the jig, and the lower jaw gripped the free coronal part of each post.

Tensile force was applied at a head rate of 0.02 in/min and a chart rate of 1 in/min until the post was dislodged from its channel. Applied tensile forces were recorded for each sample for analysis.

According to the experimental design, data from the retention study was statistically analyzed using an analysis of variance (ANOVA) test. A student-Newman-Keuls (SNK) test was also conducted to determine if statistically significant difference exists among the means values of the various groups.

The silicoated Boston post group B7, which was cemented with the Boston post cement after the channel walls were treated by method 2 demonstrated the highest retentive mean values of all the groups. The mean tensile force required for post dislodgement in that group was 172 pounds. Table 7 shows the mean separation load values for all Boston post groups.

TABLE 7

Mean separation load and standard deviation for Boston post groups

| Group | Surface Treatment | Smeared Layer | Cement | Mean | Standard Deviation |
|---|---|---|---|---|---|
| B1 | — | Intact | $ZnPo_4$ | 84.77 | 24.52 |
| B2 | — | Method 1 | $Znpo4$ | 132.10 | 16.62 |
| B3 | — | Method 2 | $ZnPo_4$ | 113.75 | 17.87 |
| B4 | — | Intact | BP* | 62.90 | 27.95 |
| B5 | — | Method 1 | BP* | 70.90 | 21.72 |
| B6 | $SiO_x$ | Method 1 | BP* | 108.70 | 31.13 |
| B7 | $SiO_x$ | Method 2 | BP* | 172.20 | 56.14 |

*BP: Boston post unfilled resin cement

The following observations were documented as posts from each group were dislodged under separation load. When the post surfaces in groups B6 and B7 were examined visually and also evaluated by SEM, it was observed that the luting resin cement was still attached to the silicoated dislodged post. The cement was also observed to be in contact with the channel walls. This indicated a cohesive failure within the Boston post resin luting cement under tensile load.

In group B1 (smeared layer intact), when posts were dislodged, they were encapsulated with an intact attached smooth surface of zinc phosphate cement. No trace of the cement was observed in contact with the channel walls. This showed cement-dentin adhesive failure.

In groups B2 and B3 (smeared layer treated by EDTA and NaOCl), scattered areas of the zinc phosphate cement were seen attached to the channel walls and also to the serrated dislodged posts, indicating a cohesive failure.

In group B4, obvious adhesive failure between the resin and the dentinal walls was observed since the cement remained totally attached to the post.

Finally, in group B5, which met the recommendations of the Boston post manufacturer's technique for cementing, only a few scattered areas of unfilled resin were observed on the post cavity walls. Most of the cement, however, remained attached to the serrated post.

Table 8 shows a summary of the Student-Newman-Keuls test for the means separation loads of Boston post groups. The test shows a significant increase in retention value for group B7 from the other groups.

TABLE 8

Summary of Student-Newman-Keuls (SNK) test for mean separation loads of Boston post group

| SNK | Grouping | Mean | Number of Samples | Group* |
|---|---|---|---|---|
|   | A | 172.20 | 10 | B7 \| |
|   | B | 132.10 | 10 | B2 \| |
| C | B | 113.75 | 8 | B3 \| \| |
| C | B | 108.70 | 10 | B6 \| \| |
| C | D | 84.78 | 9 | B1 \| \| |
|   | D | 70.90 | 10 | B5 \| |

TABLE 8-continued

Summary of Student-Newman-Keuls (SNK) test for mean separation loads of Boston post group

| SNK | Grouping | Mean | Number of Samples | Group* |
|---|---|---|---|---|
| | D | 62.90 | 10 | B4 |

*Means within the same vertical bar are not significantly different

As in Boston post groups, the silicoated cast post group C5 (smeared layer treated by method 2 and unfilled resin used as the luting cement) obtained the highest mean retentive values. The mean separation force required to dislodge the posts of this group was 155 pounds.

Table 9 show the mean separation loads and standard deviation of all cast post groups.

TABLE 9

Mean separation loads and standard deviation for cast groups

| Group | Surface Treatment | Smeared Layer | Cement | Mean | Standard Deviation |
|---|---|---|---|---|---|
| C1 | — | Intact | ZnPo4 | 65 | 16.79 |
| C2 | — | Method 2 | ZnPo4 | 67.60 | 14.61 |
| C3 | — | Method 1 | BP* resin | 31.40 | 9.13 |
| C4 | SiO$_x$ | Method 1 | BP resin | 94.90 | 19.38 |
| C5 | SiO$_x$ | Method 2 | BP resin | 155 | 31.13 |

*Boston post unfilled resin cement

The following observations were also documented as cast posts from each group were separated from their post channel by the tensile forces.

In groups C1 and C2, as the smeared layer was either left intact or treated by method 2, examination of the post and the channel walls surfaces showed that zinc phosphate cement always remained within the post channel. No cement was attached to the dislodged posts, which indicated an adhesive failure between the zinc phosphate cement and the smooth post.

In group C3, which had the lowest retention values of all the groups, unfilled resin also remained within the post channel upon post separation, and no adhesion to the post was observed.

In groups C4 and C5, the Boston post resin was observed to be attached to the silicoated post surfaces and also to the post channel walls. It was an indication of a cohesive failure within the unfilled resin.

Table 10 is a summary of the Student-Newman-Kuels test for the mean separation loads of all cast post groups. As in the Boston post groups, SNK test shows significant statistical retention values for the silicoated cast post in group C5.

TABLE 10

Summary of Student-Newman-Keuls (SNK) test for mean separation loads

| SNK Groups | Mean | Number of Samples | Group* |
|---|---|---|---|
| A | 155 | 10 | C5 |
| B | 94.90 | 10 | C4 |
| C | 67.60 | 10 | C2 |
| C | 65.00 | 10 | C1 |
| D | 31.40 | 10 | C3 |

*Means within the vertical bar not significantly different.

When mean separation loads results of Boston posts groups and cast post groups were combined and statistically analyzed by ANOVA and SNK tests, the following results were obtained: groups B7 and C5 showed significantly higher retention values for the 12 groups; mean separation loads of group B7 were not significantly different from C5 but was significantly different from all other groups; group C3 had the lowest mean values and was significantly different from all other groups.

Figure 2:
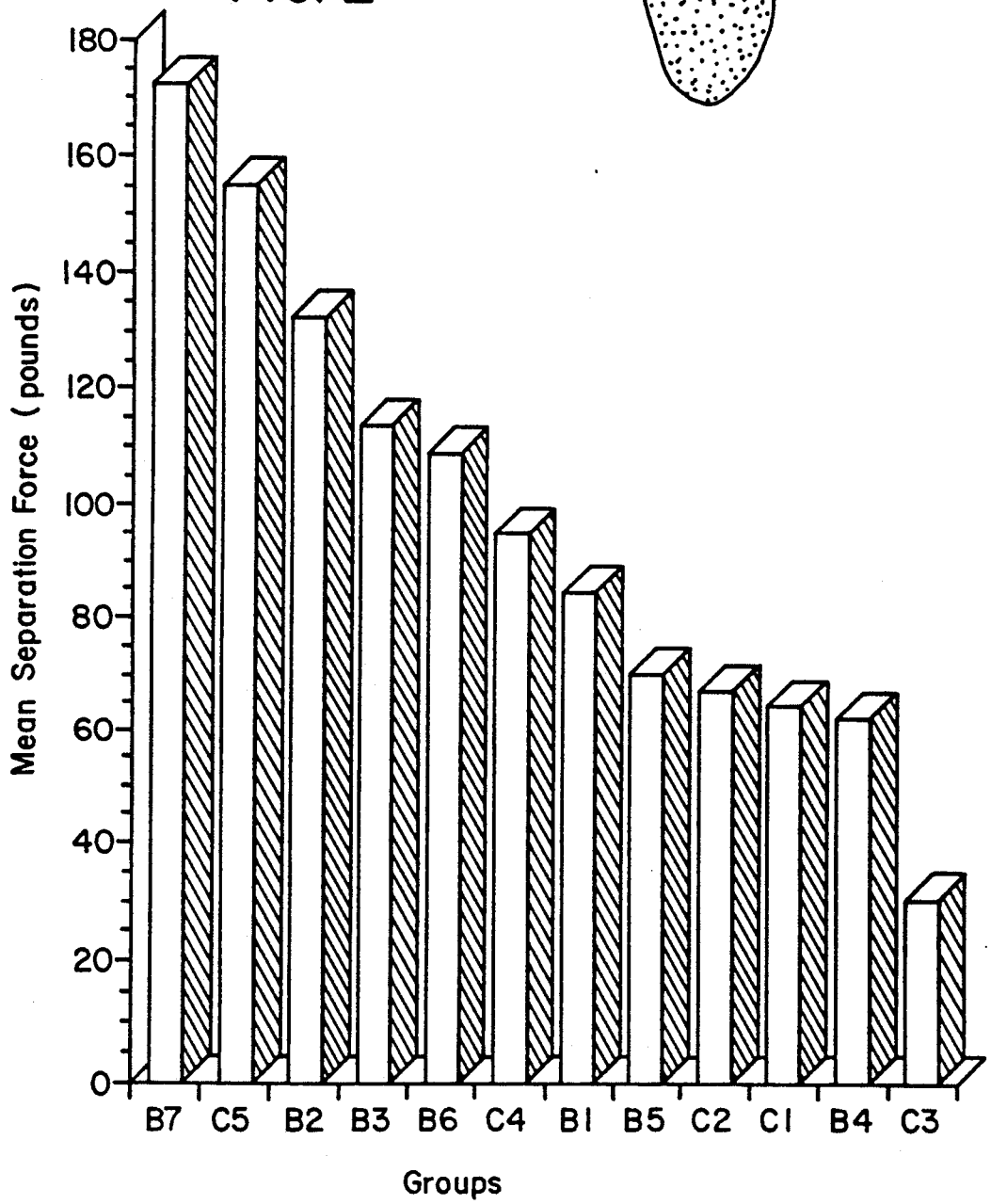
FIG. 2 is a graph illustrating the mean separation loads for all retention study groups.

Table 11 shows separation load, mean values and standard deviation of all retention study groups in decreasing order. Table 12 shows a summary of SNK test for mean separation loads of all retention study groups. FIG. 2 illustrates the mean separation loads for all retention study groups.

TABLE 11

Mean separation load and standard deviation of all retention study groups

| Group | | Surface Treatment | Smeared Layer | Cement | Mean | Standard Deviation |
|---|---|---|---|---|---|---|
| 1. Boston P. | B7 | SiO$_x$ | Method 2 | BP* Resin | 172.20 | 56.14 |
| 2. Cast P. | C5 | SiO$_x$ | Method 2 | BP Resin | 155 | 37.12 |
| 3. Boston P. | B2 | — | Method 1 | ZnPO$_4$ | 132.10 | 16.62 |
| 4. Boston P. | B3 | — | Method 2 | ZnPO$_4$ | 113.75 | 17.87 |
| 5. Boston P. | B6 | SiO$_x$ | Method 1 | BP Resin | 108.70 | 31.13 |
| 6. Cast P. | C4 | SiO$_x$ | Method 1 | BP Resin | 94.90 | 19.38 |
| 7. Boston P. | B1 | — | Intact | ZnPO$_4$ | 84.78 | 24.52 |
| 8. Boston P. | B5 | — | Method 1 | BP Resin | 70.90 | 21.72 |
| 9. Cast P. | C2 | — | Method 2 | ZnPO$_4$ | 67.60 | 14.61 |
| 10. Cast P. | C1 | — | Intact | ZnPO$_4$ | 65 | 16.79 |
| 11. Boston P. | B4 | — | Intact | BP Resin | 62.90 | 27.95 |
| 12. Cast P. | C3 | — | Method 1 | BP Resin | 31.40 | 9.13 |

TABLE 12

Summary of Student-Newman-Keuls (SNK) test for mean separation loads for all groups

| SNK | Groups | Mean | Number of Samples | Group* |
|---|---|---|---|---|
| | A | 172.20 | 10 | B7 |
| B | A | 155 | 10 | C5 |
| B | C | 132.10 | 10 | B2 |
| D | C | 113.75 | 8 | B3 |
| D | C | 108.70 | 10 | B6 |
| D | E | 94.90 | 10 | C4 |
| D | E | 84.78 | 9 | B1 |
| | E | 70.90 | 10 | B5 |
| | E | 67.60 | 10 | C2 |
| | E | 65 | 10 | C1 |
| | F | 31.40 | 10 | C3 |

*Means within the same vertical bar are not significantly different

In the retention study groups it was shown that irregularities in both interfaces increased the retention of the serrated post when luted with zinc phosphate or unfilled resin. The chemical bond between the silicoated metal surface and unfilled resin and also the bonding between resin an dentin showed the highest retentive values.

The strong adhesion between either silicoated post designs and resin made the metal post and luting resin work as one unit under tensile load. Therefore, the only flexibility allowed for the resin was the locked branches of the cement into the dentinal tubules. Since that penetration was successful enough to provide a strong mechanical lock, and may have achieved a chemical type of bonding in some cases, the luting cement became trapped or locked between two hard surfaces. This explains the cohesive failure in unfilled resin in the silicoated groups and when the smeared layer was removed (Groups B6, B7, C4 and C5).

The serrated passive boston post provided the luting cement with a successful mechanical lock which positively influenced the resistance of the post to dislodgement in this study. Bonding between zinc phosphate cement and dentin with the intact smeared layer in group B1 was higher than bonding between unfilled resin and dentin in group B4.

Bonding between zinc phosphate cement and metal (smooth cast post) in group C1 was significantly higher than bonding between unfilled resin and metal in group C3. This was the reason behind the significantly lower retention values of group C3 from all other samples. When a smooth cast post was tested it was shown that removing the smeared layer did not affect the post retention with zinc phosphate or resin cement. This could be because the bonding between both cements to dentin was higher than their bonds to metal in smeared or unsmeared conditions. This was observed as dislodged cast posts had no cement attachment. All the luting cement was left in the post channel (groups C1, C2 and C3).

Examination of the cast posts before and after cementation with zinc phosphate cement showed that the smooth cast post lost its shine. Its surface became rough and dull. This was probably due to the high $H_3PO_4$ acid effect on the metal surface, which may lead to the corrosion of metal posts as suggested by Angmar-Mansson et al. (1971). This was not seen with unfilled resin cement.

The retention of B2 and B3 groups was purely mechanical because the Boston post serrations and the indentations on the dental surface provided the zinc phosphate with interlocks even when the smeared layer was not removed totally by method 1. In fact, the retention of zinc phosphate with the smeared layer partially removed was better in group B2 than the total smeared layer removal in B3. This may have been because of the difference in roughness between the smeared component and the dentinal surface, which could have provided a better interlock for the zinc phosphate cement than its interlock with the dentinal tubule orifices on the smoother surface alone.

This was not the case with unfilled resin because it was not capable of generating high retentive values when mechanical means alone were used on both interfaces. For group B5, which also represents the boston post technique in every condition, the mean tensile strength was 70.0 lbs. In fact, it was surprising to find that zinc phosphate, when tested under the same conditions, had a retention value twice that of the unfilled resin (132 lbs). This can be explained by the higher modulus of elasticity of the unfilled resin, which might have allowed some movement of the post and led to the sliding of the metal post away from the interlocked unfilled resin. The lower modulus of elasticity of zinc phosphate cement might have influenced its interlock in both interfaces.

The highest retention values were obtained when a successful chemical bond was achieved between the silicoated post and unfilled resin, and the smeared layer was successfully removed by means of method 2. The highest retentive values were obtained accordingly among all other groups. This was the situation with groups B7 and C5, which were not significantly different from each other. These results showed that the post design had no effect on the retention of the post because B7 was represented by the serrated Boston post and C5 was totally smooth cast post. In these two groups cohesive failure within the resin was observed in almost all the sample. This finding agrees with the results of other studies regarding the successful bonding mechanism obtained through the silicoating technique.

Figure 16:
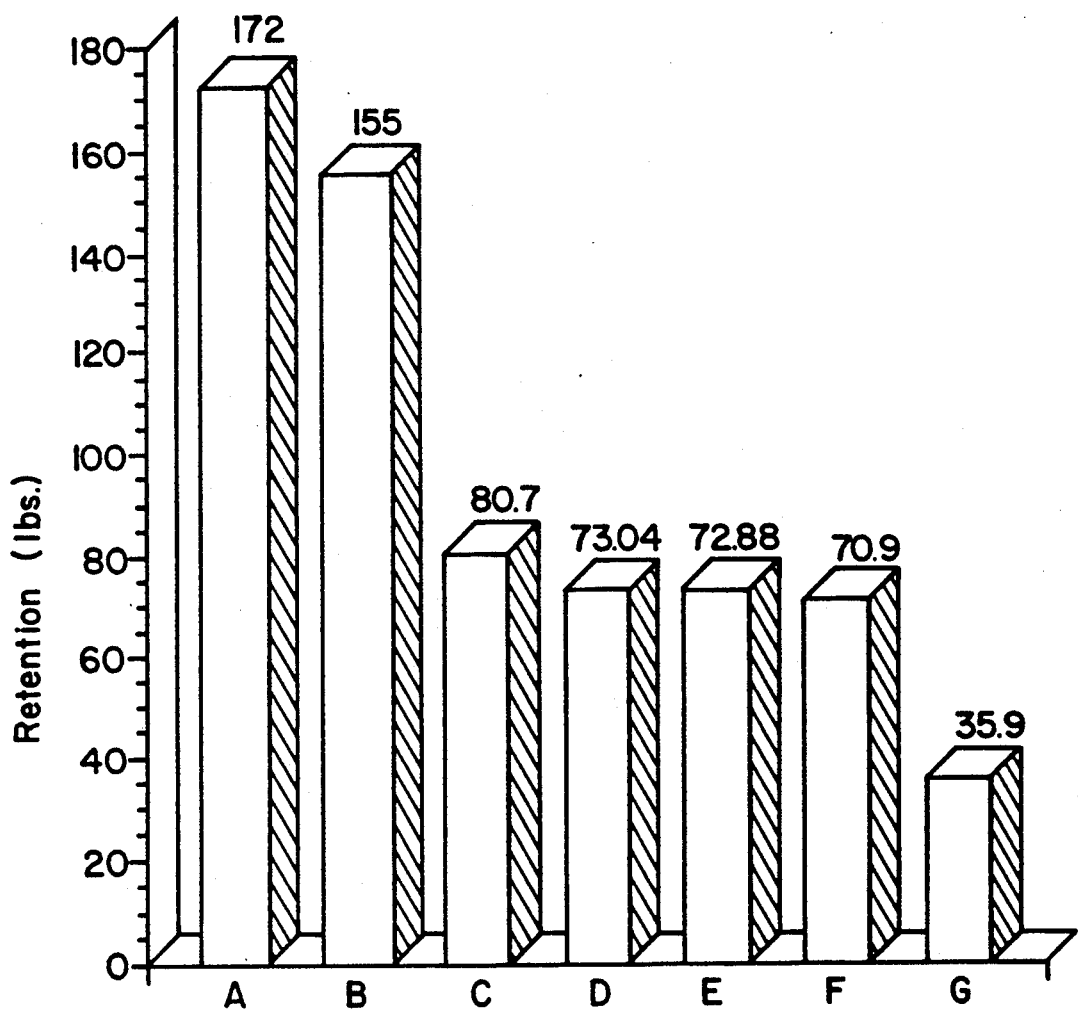
FIG. 16 illustrates a graph of the retention values of an embodiment of the invention compared to conventional passive post systems, all at 7 mm depth.

The retention achieved in this study for a silicoated parallel-sided passive post cemented with unfilled resin (155–172 lbs) was significantly higher than any other passive post system tested in other studies. FIG. 16 shows the retention values of passive posts from several studies compared to the silicoated posts retention values of this study, all at 7 mm depth. In particular, A is SiOx—C Boston Post (this study (B7));
B is SiOx—C Smooth Cast Post (this study (c5));
C is Boston Post (Nathanson (1988));
D is Parapost (Assif & Ferber (1982));
E is Parapost (Johnson (1978));
F is Boston Post (this study);
G is Parapost (Nathanson (1988)).

In fact, the retention of silicoated passive post in this study, cemented at 7-mm depth, was not significantly different from the retention of the active parallel-sided and threaded post, cemented at 8 mm, Standlee et al. (1978).

Another advantage of silicoating metal posts is the resistance to corrosion. If corrosion of metal posts has a considerable influence on root fracture, as reported by several studies, then the corrosion-resistant silicoated surface can help by eliminating another possible factor.

Scanning Electron Microscopic Study

Examination by scanning electron microscopy (SEM) was performed to evaluate the condition of intact smeared layer covering the post cavity preparation without any chemical treatment, comparison between methods 1 and 2 (of the post Retention Study) in their effectiveness in removing the smeared layer, and the penetration of Boston post resin cement into the dentinal tubules.

Seventeen single rooted anterior, freshly extracted teeth were collected, and stored in physiological saline. The crowns of these teeth were removed at the cemento-enamel junction and the samples were divided into the following divisions.

Division I

Two samples were used to evaluate the condition of the intact smeared layer after a root canal treatment was performed and the post channel was created.

A separating disc was used to make, two longitudinal shallow groove on the outer surface of the root. At this point, a spatula was forced into the grooves to facilitation splitting of the root into two segments.

Division II and III

Four samples were also used to evaluate the surfaces treated by (EDTA) and (NaOCl). Two specimens were used to evaluate the effectiveness of smeared layer removal by method 1 and 2. The four samples were sectioned as in previous divisions.

Divisions IV, V and VI

Nine samples were separated equally into 3 divisions, representing groups B4, B5, and B7 in the retention study, to deal with treatment of the smeared layer, type of post and luting cement. Division IV represented group B4, division V represented group B5, and division VI represented group B7.

Twenty-four hours after cementation, all samples were thermocycled as in the retention study. Samples then were placed in a 5% solution of nitric acid for 48 hours, until the inorganic material of the teeth was dissolved. They were then placed in a 5.25% solution of sodium hypochlorite for another 48 hours until the organic material was dissolved. The specimens were left to air dry. Each specimen was examined at 30X magnification before preparation for SEM evaluation.

Division VII

Two samples were prepared as in group B7, then mounted in clear acrylic resin. An Isoment cutting machine was employed to make two longitudinal sections in each sample, first at 1 mm from the cemented post and then 2 mm away. The four sectioned layers were etched in 17% EDTA from 3 minutes then in 5.25% NaOCl for 1 min.

Table 5 explains the experimental design of all previous divisions for the SEM study. Samples from all previous divisions were mounted on SEM stubs using conductive silver paint and then stored in a desiccator for two days before being sputter coated with 25 nanometers of gold alloy. All samples were then examined by SEM.

TABLE 5

| Division | Samples | Type | Sample Preparation |
|---|---|---|---|
| I | 2 | No treatment for smeared layer | Split in two |
| II | 2 | Smeared layer treated by method 1 | Split in two |
| III | 2 | Smeared layer treated by method 2 | Split in two |
| IV | 3 | Represents group B4 in post retention study | Place samples in 5% HNO3 for 48 hrs, then in 5.25% NaOCl for 48 hrs then mount |
| V | 3 | Represents group B5 in post retention study | Place samples in 5% HNO3 for 48 hrs, then in 5.25% NaOCl for 48 hrs then mount |
| VI | 3 | Represent group B7 in post retention study | Place samples in 5% HNO3 for 48 hrs, then in 5.25% NaOCl for 48 hrs then mount |
| VII | 2 | Represents group B7 in post retention study | Longitudinal sections 1 mm and 2 mm away from post then etched by EDTA and NaOCl |

Division I

All post cavity preparation walls were covered with a smeared layer in this division. No dentinal tubule orifices were detected along the post channel. FIG. 3 shows an SEM of a smeared layer on post channel wall after post cavity preparation, original magnification at X1000. No dentinal tubules are exposed.

Division II

Post channel walls in this division were treated by method 1, as recommended by the manufacturers of the Boston post system to remove the smeared layer. SEM observation showed that the smeared layer was partially removed in this division. FIG. 5 shows an SEM of a partially removed smeared layer on the post channel wall after treatment by method 1, original magnification at X700. FIG. 6 shows the same as FIG. 5, but at magnification X1000. Some areas along the channel walls showed exposure of the dentinal tubules' orifices, while other areas remained covered with the smeared layer or showed dentinal orifices still fully or partially occluded with debris. In summary the smeared layer in this division was not removed successfully and the lumens of the dentinal tubules were still blocked most of the time with debris.

Division III

Post cavity preparation walls in this division were treated by the modified method 2 according to the present invention. SEM examination showed that the smeared layer in this division was successfully removed from most areas along the post channel. FIG. 4 is an SEM of the successful removal of the smeared layer, magnification at X900. The orifices of the dentinal tubules were clearly open and free of any debris. However, some areas continued to be partially occluded. This occurred in less than 10% of the total surface.

Division IV, V and VI

Figure 7:
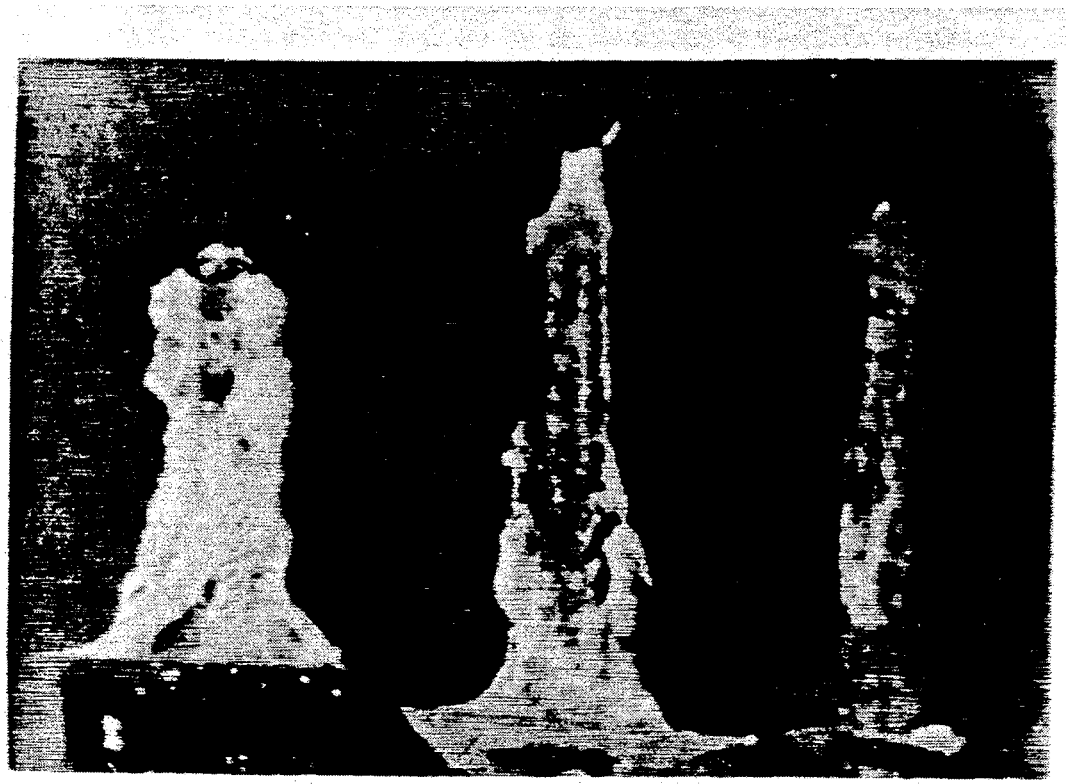
FIG. 7 is a photograph showing the penetration of unfilled resin into dentin after the teeth were dissolved using 5% HNO3 for 48 hours followed by 5.25% NaOCl for an additional 48 hours.

In these divisions, the tooth structure was completely dissolved and depth of penetration of the unfilled resin was observed directly, and, later, by lower magnification, then by the SEM. FIG. 7 is a photograph showing the penetration of unfilled resin into dentin after the teeth were dissolved using 5% HNO3 for 48 hours followed by 5.25% NaOCl for an additional 48 hours. From right to left: smeared layer left intact, smeared layer treated by method 1, and smeared layer removed by method 2.

In division IV, when the smeared layer remained intact, as in the group B4 (in the retention study), unfilled resin was found to be attached to the post surface and no evidence of any resin penetration into the dentinal tubules was observed. Probably the smeared layer acted here as a barrier to the flow of the resin beyond the borders of the post channel.

In division V, resin tags were observed protruding from the post and obviously penetrating into the dentinal tubules, although the penetration was not uniform. Some areas showed remarkable resin penetration (mostly seen at the cervical level), while other areas showed less penetration. On the apical third of the post no resin tags were observed in any of the samples. FIG. 8 is an SEM showing limited penetration of resin tags (tooth dissolved by using 5% HNO3 and 5.25% NaOCl) after the smeared layer was treated by using method 1, original magnification at X740. This finding reflected the inadequate removal of the smeared layer by method 1, as observed in division II.

In division VI, there was a remarkably uniform penetration of unified resin into the dentinal tubules. FIGS. 10 and 11 are SEMs of the successful penetration of unfilled resin tags (tooth dissolved by using 5% HNO3 and 5.25% NaOCl) into the dentinal tubules after the smeared layer was removed using method 2 and the specially designed high vacuum suction tip was used to dry the post cavity, original magnification at X600 for FIG. 10 and X1000 for FIG. 11. Resin tags were extended close to the borders of the cementum at the cervical level. All surfaces of the cemented post were covered with resin tags, although very few areas showed shallow penetration. The finding reflected the successful removal of the smeared layer, as observed in division II. Depth of resin penetration decreased in a liner fashion from the cervical level to the apical level of the post surface. FIG. 9 is an SEM showing the variable depth of penetration of resin tags (tooth dissolved by using 5% HNO3 and 5.25% NaOCl) after smeared layer was removed by using method 2 and post cavity was not dried using the specially designed high vacuum suction tip. The post cavity was dried using paper points and compressed air, original magnification at X100. FIG. 10 illustrates the same as FIG. 9 except at magnification X600. FIG. 11 illustrates the same as FIG. 9 except at magnification X1000. FIGS. 12 and 13 are SEMs showing resin tags penetration on the apical third of a Boston post on a partially dissolved tooth, the smeared layer was removed by method 2. FIG. 12 shows areas of shallow penetration of resin on the apical third, original magnification at X180. FIG. 13 shows bridges of resin tags between the unfilled resin luting cement and dentin, original magnification at X760.

Division VII

FIGS. 14 and 15 are SEMs showing the occupation of dentinal tubules by resin tags at variable depths from the post cavity. FIG. 14 is a sectional layer 1-mm away from the post channel, which showed resin tags filling the lumens of the dentinal tubules in several areas along the root, original magnification at X1000. FIG. 15 is a sectional layer 2-mm away from the post channel and approximately 0.3 mm from the dentinal-cementum junction, which showed resin tags continued to occupy the lumens of the dentinal tubules, mostly in the cervical level, original magnification at X600. In general, these dentinal tubules occupied with resin were less than those observed in the 1-mm section.

Reinforcement Study

Samples of the reinforcement study were subjected to compression forces applied directly to the outer body of the tooth at the coronal level of the root. Continuous load was introduced until the samples had fractures. Resistance of each sample to fracture was documented and later compared in a statistical manner.

Eighteen freshly extracted, single-rooted anterior teeth were collected and stored immediately in physiological saline. Selection of these teeth was based on collecting at least one pair of symmetrically shaped teeth from the same patient (i.e., right and left centrals or right and left canines). All samples were inspected to guarantee absence of carries, fracture or resorption.

Attached calculus, soft tissue and bone were removed from each tooth. The eighteen teeth were divided into 9 groups. Each group contained a right and left tooth of the same category, collected from the same patient.

A straight circumferential line was drawn at the level of the cemento-enamel junction of each tooth. This mark served as the guidance for separating each crown from its root. The separation procedure was performed using a separating disc in the presence of water spray.

A root canal procedure was performed on each sample. Then each root canal was filled as described in the retention study. A post space was created in each root by using a heated endodontic plugger and then a Boston post twist drill to create a 7 mm deep post cavity preparation. Each group was then divided into control samples and experimental samples. Table 6 shows the experimental design for reinforcement study.

Control samples were prepared by cementing the Boston posts (1.6 mm diameter) into their prepared channels to a depth of 7 mm using zinc phosphate cement. The smeared layer on the channel walls was left intact. The control samples in this study represented the group B1 in the retention study.

TABLE 6

| Experimental design for reinforcement study | | | | |
|---|---|---|---|---|
| | Number of Samples | Post | Cement | Surface Tax | Smeared Layer |
| Control Samples | 9 | Boston | ZnPO4 | Non | intact |
| Experiment Samples | 9 | Boston | Unfilled Resin | (SiO$_x$) | Removed by method 2 |

Nine silicoated Boston posts were cemented into their prepared channels using Boston post resin cement. Before cementation the smeared layer on channel walls was treated by method 2. The experimental samples in this study represented the group B7 in the retention study. Samples from all groups were thermocycled in water 500 times at temperature of 8° C. to 50° C. at dwell time of 15 seconds.

To distribute the compression load evenly to the tooth structure and also to prevent the sample from sliding under the increased load, it was necessary to make two smooth surfaces on the root parallel to each other before testing. Control and test samples from each group were positioned in a box-shaped matrix at the same angle and then surrounded with light-cured composite resin. First the samples were checked for the same degree of position using the side walls of the box as a landmark. The composite resin filled matrix was then placed in a Dentacolor (Kulzer Inc., Irvine, CA) photocure device and cured for 90 seconds. Each sample was then removed from the plastic box and surfaced using standard metallographic techniques.

Samples from each group were ground from the buccal and the lingual side until the composite resin was removed, a smooth dentinal surface was exposed, and the buccal and lingual sides became parallel to each other. Caution was taken to remove the same amount of tooth structure during grinding of samples from each group. Next a measuring device was used to guarantee exact thickness of each sample from the same group and make the necessary adjustments. A guiding brass block was used to aid in keeping the right angulation of each sample during grinding. The coronal edge around the post of each sample was painted with methylene blue to help in early detection of crack lines.

Each sample was placed on a compression cell in an Instron Universal testing machine on the ground buccal or lingual side. Next a smoothed-tip rod (4.5×6 mm diameter) was attached to the Instron machine and positioned to contact the top surface of the sample vertically, starting from the coronal edge.

The amount of the applied load to each sample was recorded. The compressive load was applied at a head rate of 0.02 in/min and a chart rate of 5 in/min was used. The load was applied constantly until the tooth cracked or fractured, and data from all samples were collected for analysis.

Data from the reinforcement study was statistically analyzed by using randomized complete block analysis of variance and by paired t-test.

Compression tests on all experimental groups showed higher resistance to fracture than the control groups. The mean difference between the experimental samples and the control samples for all 9 groups was 61.1 pounds increase for experimental groups.

Results of randomized complete block analysis of variance indicated that the affect of the group (p-value=0.0001) and the effect of the treatment (p-value=0.0040) were both statistically significant. In other words, when corrected for variation in the teeth specimens, the treatments (control vs. experimental) were significantly different. Table 13 shows compression test values for all groups.

TABLE 13

Results of compression tests in all groups

| Group | Sample Thickness | Control Sample | Experiment Sample | Strength Difference |
|---|---|---|---|---|
| 1 | 5.0 mm | 620 | 680 | 60 |
| 2 | 5.0 mm | 550 | 580 | 30 |
| 3 | 7.0 mm | 450 | 470 | 20 |
| 4 | 5.5 mm | 430 | 525 | 95 |
| 5 | 4.5 mm | 180 | 220 | 40 |
| 6 | 4.5 mm | 280 | 300 | 20 |
| 7 | 4.0 mm | 230 | 350 | 120 |
| 8 | 4.0 mm | 100 | 240 | 140 |
| 9 | 4.0 mm | 255 | 280 | 25 |
| (mean) | | 343.8 | 405 | 61.1 |

Reinforcement of endodontically treated teeth has been a major concern after a root canal treatment, especially for those cases where the remaining amount of root dentin is not strong enough to withstand high loads. In those cases if the tooth still has an intact clinical crown, normal filling materials like amalgam or composite might not be enough for the tooth to resist fracture. If traditional type posts were to be used, the tooth might split under the transferred forces. The issue of reinforcing endodontically treated teeth to prevent fracture should be of equal importance to the retention of the restoration. Actually, one study favored fracture of the post before it transfers the traumatic forces to the root. It suggested using a hollow post which absorbed the load and fractures before any damage occurs to the root structure, Mosen et al. (1984).

The results of the reinforcement study are of help for reinforcing endodontically treated teeth, especially those with immature roots and large pulpal canals with minimal thickness of surrounding dentin. In each experimental group in the reinforcement study an increased resistance to fracture was obtained when the unfilled resin infiltrated into the dentinal tubules. The depth of penetration of the resin was significant once the smeared layer was successfully removed. Tubular infiltration however, was affected by several factors, such as: degree of calcification and number of effected tubules; diameter of the tubules, which is related to the location in the canal and age of patient; and the amount of remaining moisture within the tubule which could resist the flow of the resin. The last factor would seem to be the most influential for resin penetration.

In this study, teeth were moistened continuously to prevent dehydration. The effect of the design suction tip and compressed air probably help in evacuating the moisture from the dentinal tubules. This evacuation was enough to clear the way for the resin to penetrate the tubules, with other factors being the current created by the rotating lentulo spiral, the pressure of post insertion and the capillarity of dentinal tubules.

In the SEM study, it was shown that unfilled resin penetration was most successful in the cervical level of the root, most likely because of the large diameter and the intensity of the tubules in that region. This penetration was observed to reach 2 mm away from the post channel walls and neighboring the cement borders. This region appears to have the greatest need for reinforcement, because it has less periodontal support, larger tubules and less dentinal thickness. All of these are important because most traumatic forces are directed to the cervical level of the root.

Figure 17:
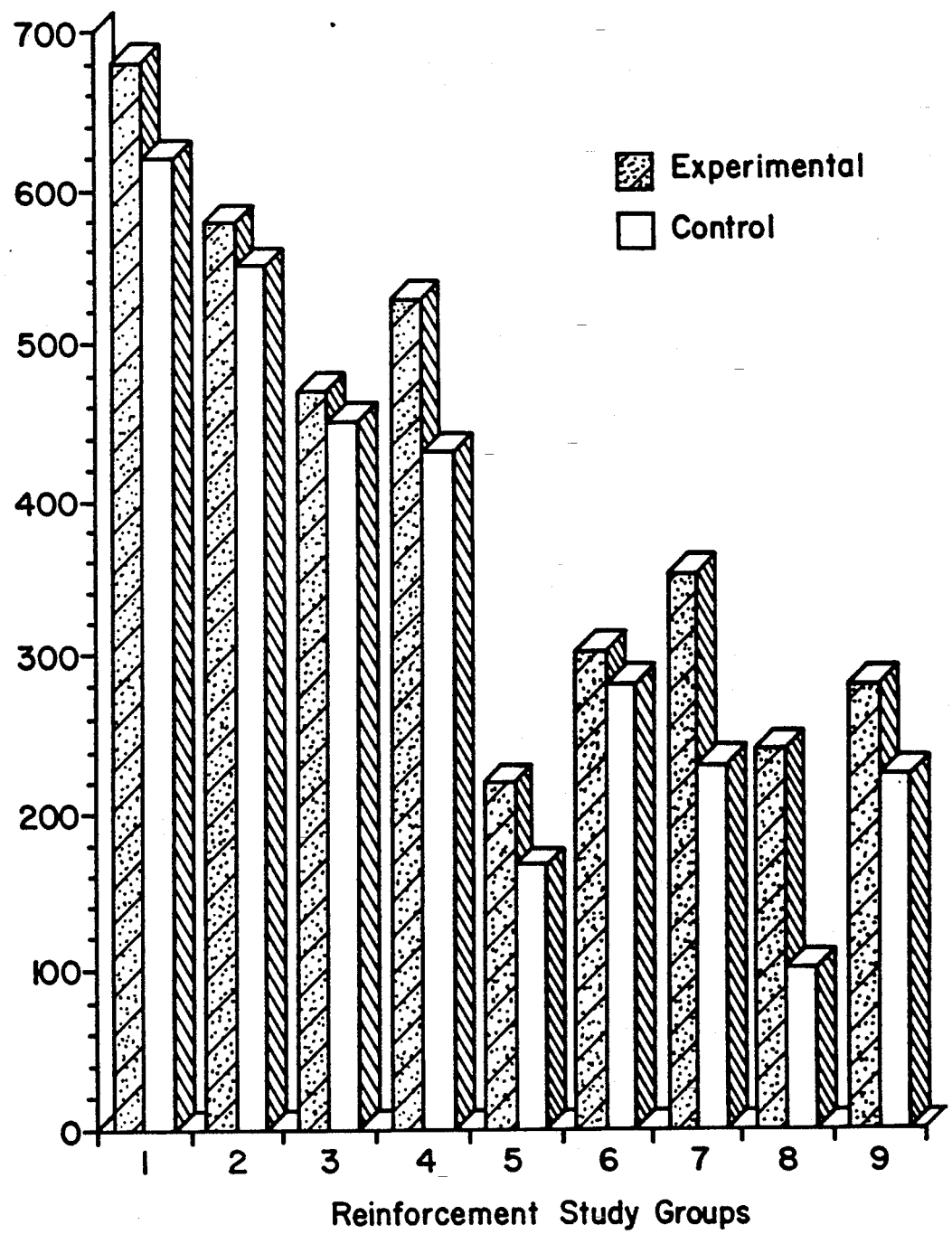
FIG. 17 illustrates a graph of the reinforcement study groups.

When considering the differences between experimental and control samples, the experimental samples exhibited a significantly higher strength. FIG. 17 illustrates the reinforcement study groups. Specifically, the experimental samples showed a 30.3% increase resistance to fracture. A paired t-test was found to be significant. Table 14 shows these values.

TABLE 14

Differences between experimental and control groups

| Variable | Mean | Standard Deviation | Significant Difference | P-Value |
|---|---|---|---|---|
| Difference (Pounds) | 61.1 | 46.0 | yes | 0.0040 |
| % difference | 30.3 | 43.8 | yes* | 0.0711 |

*significant at 0.10, not at 0.05

The use of Bis-GMA based unfilled resin as a luting agent, which bonds to a silicoated metal post and also penetrates the denial tubules, was investigated in this study to study its effectiveness in the reinforcement of endodontically treated teeth and to obtain maximum retention for the post system. The following results were obtained.

Successfully removing the smeared layer and minimizing the amount of moisture in the dentinal tubules are important factors that increase the infiltration of an unfilled resin with low viscosity into the tubules, resulting in a surprising reinforcement of the tooth structure of up to 30.3%. Compression test results showed significant increase resistance to fracture in the body of the tooth whenever this technique was applied. The successful deep penetration of the resin was observed by scanning electron microscopic examination.

Silicoating the post surface significantly increased the retention of the post when the smeared layer was adequately removed and unfilled resin used as the luting agent. Under tensile loading, cohesive failure within the resin was demonstrated, thus confirming the successful adhesive bonding between the metal surface and resin through the silicoated and silanated layers. This method showed the highest retention values for a passive post design compared with results from other passive post systems in the literatures.

The shape of the post surface was not an important factor for the improved retention of the post when it was silicoated and bonded to resin. In fact the retention of a serrated Boston post and a totally smooth cast post was not significantly different when they were treated in a similar manner.

Parallel-sided, serrated Boston post design was much more retentive than the smooth parallel-sided cast post when zinc phosphate cement was used as the luting agent. This result occurred because the Boston post provided the cement with mechanical interlocks.

The Boston post system itself did not provide superior retention values when the recommended unfilled resin was used as a luting agent. In fact, poor adhesion to the post by the resin was observed, which could have lowered the retention values of the system.

The bonding of either zinc phosphate cement or resin cement to the chamber walls was higher than bonding to the smooth cast posts, with or without removal of the smeared layer.

The bond strengths of zinc phosphate cement to the metal surface is appreciably higher than that of the unfilled resins' bond to metal.

If a strong mechanical or chemical adhesion was obtained on the post-cement interface, removal of the smeared layer significantly increased post retention with both zinc phosphate and unfilled resin.

While the invention has been described in detail and with reference to specific embodiment thereof, it is apparent to one skilled in the art that various changes and modification can be made therein without departing from the spirit and scope thereof.

What is claimed is:

1. Method of mounting a passive metal post in a tooth comprising the steps of:
    silicoating said post;
    generating a post channel;
    irrigating said post channel with about 1.5 ml of a first solution comprising about 17% Ethylene Diamine Tetracetic Acid having a pH of about 7.5 for about 1 minute;
    irrigating said post channel with about 1.5 ml of said first solution for about 1 minute;
    irrigating said post channel with about 2 ml of said first solution for about 1 minute;
    irrigating said post channel with a second solution comprising about 5.25% Sodium Hypochloride for about 2 minutes;
    evacuating said post channel:
    injecting a cement comprising chemical curer Bis-GMA and TEGDMA based, unfilled resin having a high compressive strength value and a low viscosity value into said post channel;
    inserting said silicoated post into said post channel;
    holding said post under pressure until said cement is set, thereby mounting said passive post.

2. The method of claim 1, further comprising the step of distributing said cement with a Lentulo spiral in said post channel which helps said cement penetrate into dentinal tubules.

3. The method of claim 1, further comprising the step of evacuating said post channel with a vacuum using a high vacuum suction tip having an outer diameter less than the inner diameter of said post channel.

4. The method of claim 1, further comprising the step of irrigating said post channel with compressed air.

5. The method according to claim 1, wherein the passive post comprises a shaft part having a hexagonal shape with each of six sides being parallel to a long axis of said shaft part and a coronal part.

6. The method according to claim 5, wherein a central part of said coronal part has a groove which is parallel to a long axis of said shaft part, said groove being open to a top surface of said coronal part, and said groove is threaded to accept a threaded shaft.

7. The method according to claim 5, wherein a diameter of said coronal part is larger than a diameter of said shaft part.

8. The method according to claim 5, wherein a total length of said post is about 12 mm to 20 mm.

9. The method according to claim 5, wherein said coronal part is about 5 mm to 7 mm of a total length of said post and said coronal part has a diameter of about 1 mm to 2 mm greater than a diameter of said shaft part.

10. A passive post for use as a solid foundation in endodontically treated teeth comprising:
    a shaft part having a hexagonal shape with each of six sides being parallel to a long axis of said shaft part; and
    a coronal part;wherein substantially the entire surface of said post is silicoated.

11. The passive post according to claim 10, wherein a central part of said coronal part has a groove which is parallel to a long axis of said shaft part, said groove being open to a top surface of said coronal part, and said groove is threaded to accept a threaded shaft.

12. The passive post according to claim 11, wherein a diameter of said coronal part is larger than a diameter of said shaft part.

13. The passive post according to claim 10, wherein a total length of said post is about 12 mm to 20 mm.

14. The passive post according to claim 10, wherein said coronal part is about 5 mm to 7 mm of a total length of said post and said coronal part has a diameter of about 1 mm to 2 mm greater than a diameter of said shaft part.

* * * * *